US009816981B2

(12) United States Patent
Sawa et al.

(10) Patent No.: US 9,816,981 B2
(45) Date of Patent: *Nov. 14, 2017

(54) ALKYNYL SUGAR ANALOGS FOR LABELING AND VISUALIZATION OF GLYCOCONJUGATES IN CELLS

(75) Inventors: Masaaki Sawa, Ibaraki (JP); Chi-Huey Wong, Taipei (TW); Tsui-Ling Hsu, Taipei (TW); Sarah Hanson, San Marcos, CA (US)

(73) Assignee: ACADEMIA SINICA, Taipei (TW)

( * ) Notice: Subject to any disclaimer, the term of this patent is extended or adjusted under 35 U.S.C. 154(b) by 859 days.

This patent is subject to a terminal disclaimer.

(21) Appl. No.: 13/159,339

(22) Filed: Jun. 13, 2011

(65) Prior Publication Data

US 2012/0149887 A1    Jun. 14, 2012

Related U.S. Application Data

(62) Division of application No. 12/079,226, filed on Mar. 24, 2008, now Pat. No. 7,960,139.

(60) Provisional application No. 60/896,777, filed on Mar. 23, 2007.

(51) Int. Cl.
| | |
|---|---|
| *C07H 15/04* | (2006.01) |
| *C07H 19/10* | (2006.01) |
| *G01N 33/50* | (2006.01) |
| *G01N 33/533* | (2006.01) |

(52) U.S. Cl.
CPC ..... *G01N 33/5005* (2013.01); *G01N 33/5008* (2013.01); *G01N 33/533* (2013.01); *G01N 2400/00* (2013.01)

(58) Field of Classification Search
CPC ............. G01N 33/5005; G01N 33/533; G01N 33/5008; G01N 2400/00
See application file for complete search history.

(56) References Cited

U.S. PATENT DOCUMENTS

| | | |
|---|---|---|
| 3,773,919 A | 11/1973 | Boswell et al. |
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,975,278 A | 12/1990 | Senter et al. |
| 5,004,697 A | 4/1991 | Pardridge |
| 5,112,596 A | 5/1992 | Malfroy-Camine |
| 5,122,469 A | 6/1992 | Mather et al. |
| 5,229,275 A | 7/1993 | Goroff |
| 5,264,365 A | 11/1993 | Georgiou et al. |
| 5,268,164 A | 12/1993 | Kozarich et al. |
| 5,395,541 A | 3/1995 | Carpenter et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,580,717 A | 12/1996 | Dower et al. |
| 5,587,458 A | 12/1996 | King et al. |
| 5,591,669 A | 1/1997 | Krimpenfort et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,677,180 A | 10/1997 | Robinson et al. |
| 5,686,416 A | 11/1997 | Kozarich et al. |
| 5,733,743 A | 3/1998 | Johnson et al. |

(Continued)

FOREIGN PATENT DOCUMENTS

| | | |
|---|---|---|
| EP | 404097 A2 | 12/1990 |
| EP | 1391213 A1 | 2/2004 |

(Continued)

OTHER PUBLICATIONS

Fernandez-Megia et al. A click approach to unprotected Glycodendrimers 2006, vol. 39, pp. 2113-2120.*
Sawa et al. Glycoproteomic probes for fluorescent imaging of fucosylated glycans in vivo. PNAS 2006, vol. 103, No. 33, pp. 12371-12376.*
Hsu et al. Alkynyl sugar analogs for the labeling and visualization of glycoconjugates in cells. PNAS 2007, vol. 104, No. 8, pp. 2614-2619.*
Lee et al. Analogs of cell surface carbohydrates. Synthesis of D-galactose derivatives having an ethynyl, vinyl or epoxy residue at C-5. Carbohydrate Research 1988, vol. 176, pp. 59-72.*

(Continued)

*Primary Examiner* — Shafiqul Haq
(74) *Attorney, Agent, or Firm* — Duane Morris LLP; Vicki G. Norton; Johann Lin

(57) ABSTRACT

Methods for metabolic oligosaccharide engineering that incorporates derivatized alkyne-bearing sugar analogs as "tags" into cellular glycoconjugates are disclosed. Alkynyl derivatized Fuc and alkynyl derivatized ManNAc sugars are incorporated into cellular glycoconjugates. Chemical probes comprising an azide group and a visual or fluorogenic probe and used to label alkyne-derivatized sugar-tagged glycoconjugates are disclosed. Chemical probes bind covalently to the alkynyl group by Cu(I)-catalyzed [3+2] azide-alkyne cycloaddition and are visualized at the cell surface, intracellularly, or in a cellular extract. The labeled glycoconjugate is capable of detection by flow cytometry, SDS-PAGE, Western blot, ELISA, confocal microscopy, and mass spectrometry.

9 Claims, 16 Drawing Sheets

(56) References Cited

U.S. PATENT DOCUMENTS

| | | | |
|---|---|---|---|
| 5,736,137 A | 4/1998 | Anderson et al. | |
| 5,821,337 A | 10/1998 | Carter et al. | |
| 5,837,234 A | 11/1998 | Gentile et al. | |
| 5,840,523 A | 11/1998 | Simmons et al. | |
| 5,869,046 A | 2/1999 | Presta et al. | |
| 6,004,940 A | 12/1999 | Marasco et al. | |
| 6,027,888 A | 2/2000 | Georgiou et al. | |
| 6,083,715 A | 7/2000 | Georgiou et al. | |
| 6,265,150 B1 | 7/2001 | Terstappen et al. | |
| 6,329,173 B1 | 12/2001 | Marasco et al. | |
| 6,528,286 B1 | 3/2003 | Ryll | |
| 6,703,019 B1 | 3/2004 | Malfroy-Camine | |
| 6,824,780 B1 | 11/2004 | Devaux et al. | |
| 6,984,630 B1 | 1/2006 | Descamps et al. | |
| 7,090,973 B1 | 8/2006 | Breton | |
| 7,151,164 B2 | 12/2006 | Hansen et al. | |
| 7,943,330 B2 * | 5/2011 | Wong et al. | 435/7.21 |
| 7,960,139 B2 * | 6/2011 | Sawa et al. | 435/41 |
| 8,101,179 B2 | 1/2012 | Numazaki et al. | |
| 2002/0025313 A1 | 2/2002 | Micklus et al. | |
| 2002/0038086 A1 | 3/2002 | Hynynen et al. | |
| 2002/0065259 A1 | 5/2002 | Schatzberg et al. | |
| 2003/0073713 A1 | 4/2003 | Schoenhard | |
| 2003/0083299 A1 | 5/2003 | Ferguson | |
| 2003/0104402 A1 | 6/2003 | Zauderer et al. | |
| 2003/0118592 A1 | 6/2003 | Ledbetter et al. | |
| 2003/0129186 A1 | 7/2003 | Beliveau et al. | |
| 2003/0162695 A1 | 8/2003 | Schatzberg et al. | |
| 2003/0175884 A1 | 9/2003 | Umana et al. | |
| 2004/0072290 A1 | 4/2004 | Umana et al. | |
| 2004/0131692 A1 | 7/2004 | Kreuter et al. | |
| 2004/0204354 A1 | 10/2004 | Nelson et al. | |
| 2005/0089473 A1 | 4/2005 | Black et al. | |
| 2005/0106108 A1 | 5/2005 | Leung et al. | |
| 2005/0123546 A1 | 6/2005 | Umana et al. | |
| 2005/0124533 A1 | 6/2005 | Schatzberg et al. | |
| 2006/0073122 A1 | 4/2006 | Koezuka et al. | |
| 2006/0073161 A1 | 4/2006 | Breton | |
| 2007/0224189 A1 | 9/2007 | Lazar et al. | |
| 2007/0238871 A1 | 10/2007 | Tsuji et al. | |
| 2009/0285837 A1 | 11/2009 | Kao et al. | |
| 2010/0173323 A1 | 7/2010 | Strome | |
| 2011/0263828 A1 | 10/2011 | Wong et al. | |
| 2012/0171201 A1 | 7/2012 | Sapra | |
| 2012/0178705 A1 | 7/2012 | Liang et al. | |
| 2012/0226024 A1 | 9/2012 | Wang et al. | |
| 2013/0230886 A1 | 9/2013 | Votsmeier et al. | |
| 2013/0337018 A1 | 12/2013 | Fox | |
| 2014/0086916 A1 | 3/2014 | Zha | |
| 2014/0127241 A1 | 5/2014 | Leuschner et al. | |

FOREIGN PATENT DOCUMENTS

| | | |
|---|---|---|
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 93/01161 A1 | 1/1993 |
| WO | WO 93/06213 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/17852 A1 | 5/1997 |
| WO | WO 98/02463 A1 | 1/1998 |
| WO | WO 98/24893 A2 | 6/1998 |
| WO | WO 99/57134 A1 | 11/1999 |
| WO | WO 03/068821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/103404 A1 | 12/2004 |
| WO | WO 2005/044859 | 5/2005 |
| WO | WO 2005/103081 A2 | 11/2005 |
| WO | WO 2006/126069 A2 | 11/2006 |
| WO | WO 2006/130458 A2 | 12/2006 |
| WO | WO 2007/146847 A2 | 12/2007 |
| WO | WO 2011/005756 A1 | 1/2011 |
| WO | WO 2013/011347 A1 | 1/2013 |
| WO | WO 2013/120066 A1 | 8/2013 |
| WO | WO 2013/181585 A2 | 12/2013 |
| WO | WO 2015/026484 A1 | 2/2015 |

OTHER PUBLICATIONS

Prescher et al. Chemistry in living systems. Nature Chemical Biology 2005, vol. 1, No. 1, pp. 13-21.*

Fernandez-Megia et al. A click approach to unprotected glycodendrimers. Macromolecules 2006, vol. 39, pp. 2113-2120.*

Fessner et al. Enzymes in organic synthesis, short enzymatic synthesis of L-fucose analogs. Eur. J. Org. Chem 2000, pp. 125-132.*

Abrahmsén et al, "Analysis of signals for secretion in the staphylococcal protein A gene," *EMBO J.*, Dec. 30, 1985, 4(13B):3901-3906.

Altschul SF et al., "Basic local alignment search tool", *J Mol Biol.* Oct. 5, 1990;215(3):403-10.

Altschul SF, et al., "Gapped BLAST and PSI-BLAST: a new generation of protein database search programs", *Nucleic Acids Res.* Sep. 1, 1997;25(17):3389-402.

Anderson et al., "Stimulation of Natural Killer T Cells by Glycolipids", *Molecules*, May 2013, 18(12), 15662-15688.

Arié et al., "Chaperone function of FkpA, a heat shock prolyl isomerase, in the periplasm of *Escherichia coli*," *Mol. Microbiol.*, Jan. 2001, 39(1):199-210.

Bachmann, *Cellular and Molecular Biology*, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.

Baldwin et al., "Monoclonal antibodies in cancer treatment," *Lancet*, Mar. 15, 1986, 327(8481):603-605.

Barbas et al., "Assembly of combinatorial antibody libraries on phage surfaces: the gene III site," *Proc. Natl. Acad. Sci. U.S.A.*, Sep. 15, 1991, 88(18):7978-7982.

Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.

Barbas et al., "Semisynthetic combinatorial antibody libraries: a chemical solution to the diversity problem," *Proc. Natl. Acad. Sci. U.S.A.*, May 15, 1992, 89(10):4457-4461.

Barnes et al., "Methods for growth of cultured cells in serum-five medium," *Anal. Biochem.*, Mar. 1, 1980, 102(2):255-270.

Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.

Bass et al., "Hormone phage: an enrichment method for variant proteins with altered binding properties," *Proteins*, 1990, 8(4):309-314.

Beck A., "Biosimilar, biobetter and next generation therapeutic antibodies" *MAbs*. Mar.-Apr. 2011;3(2):107-10. Epub Mar. 1, 2011.

Berra et al., "Correlation between ganglioside distribution and histological grading of human astrocytomas," *Int. J. Cancer*, Sep. 15, 1985, 36(3):363-366.

Birklé et al., "Role of tumor-associated gangliosides in cancer progression," *Biochimie*, Mar.-Apr. 2003, 85(3-4):455-463.

Bobo et al., "Convection-enhanced delivery of macromolecules in the brain," *Proc. Natl. Acad. Sci. U.S.A.*, Mar. 15, 1994, 91(6) 2076-2080.

Boerner et al., "Production of antigen-specific human monoclonal antibodies from in vitro-primed human splenocytes," *J. Immunol.*, Jul. 1, 1991, 147(1):86-95.

Bothmann et al., "The periplasmic *Escherichia coli* peptidylprolyl cis,trans-isomerase FkpA. I. Increased functional expression of

(56) References Cited

OTHER PUBLICATIONS antibody fragments with and without cis-prolines," *J. Biol. Chem.*, Jun. 2, 2000, 275(22):17100-17105.
Brennan et al., "Preparation of bispecific antibodies by chemical recombination of monoclonal immunoglobulin G$_1$ fragments," *Science*, Jul. 5, 1985, 229(4708):81-83.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Brüggemann et al., "Designer mice: the production of human antibody repertoires in transgenic animals," *Year in Immunol.*, 1993, 7:33-40.
Capel PJ et al., "Heterogeneity of human IgG Fc receptors" *Immunomethods.* Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9, 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res.* 1989;52:81-149.
Clynes R, et al., "Fc receptors are required in passive and active immunity to melanoma" *Proc Natl Acad Sci U S A.* Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGκ monoclonal antibodies from a novel strain of minilocus transgenic mice," *Nature Biotechnol.*, Jul. 1996, 14(7):845-851.

Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Galfré et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2):163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [*Streptomyces plicatus*]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice 2$^{nd}$ ed., Chapter 3: Production of Monoclonal Antibodies*, 1986, pp. 59-103, Academic Press, London.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gottschling et al., "Stage-specific embryonic antigen-4 is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.

(56) References Cited

OTHER PUBLICATIONS

Hata, K. et al., "Limited Inhibitory Effects of Oseltamivir and Zanamivir on Human Sialidases," Antimicrobial Agents and Chemotherapy, vol. 52, No. 10, Oct. 2008, in 8 pages.

Hawkins et al., "Selection of phage antibodies by binding affinity. Mimicking affinity maturation," *J. Mol. Biol.*, 1992, 226(3):889-896.

Heyman, "Complement and Fc-receptors in regulation of the antibody response," *Immunol. Lett.*, Dec. 1996, 54(2-3):195-199.

Hinman et al., "Preparation and characterization of monoclonal antibody conjugates of the calicheamicins: a novel and potent family of antitumor antibiotics," *Cancer Res.*, Jul. 15, 1993, 53(14):3336-3342.

Hogrefe et al., "A bacteriophage lambda vector for the cloning and expression of immunoglobulin Fab fragments on the surface of filamentous phage," *Gene*, Jun. 15, 1993, 128(1):119-126.

Holliger et al., "'Diabodies': small bivalent and bispecific antibody fragments," *Proc. Natl. Acad. Sci. U.S.A.*, Jul. 15, 1993, 90(14):6444-6448.

Honegger et al., "Yet another numbering scheme for immunoglobulin variable domains. an automatic modeling and analysis tool," *J. Mol. Biol.*, Jun. 8, 2001, 309:657-670.

Hoogenboom et al., "By-passing immunisation: Human antibodies from synthetic repertoires of germline $V_H$ gene segments rearranged in vitro," *J. Mol. Biol.*, Sep. 20, 1992, 227(2):381-388.

Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.

Huang et al., "Carbohydrate-based vaccines with a glycolipid adjuvant for breast cancer," *Proc. Natl. Acad. Sci. U.S.A.*, Feb. 12, 2013, 110(7):2517-2522.

Hung et al., "Investigation of SSEA-4 binding protein in breast cancer cells," *J. Am. Chem. Soc.*, Apr. 24, 2013, 135(16):5934-5937.

Hurle et al., "Protein engineering techniques for antibody humanization," *Curr. Opin. Biotechnol.*, Aug. 1994, 5(4):428-433.

Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.

Jackson et al., "In vitro antibody maturation: Improvement of a high affinity, neutralizing antibody against IL-1β," *J. Immunol.*, Apr. 1, 1995, 154(7):3310-3319.

Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.

Jakobovits et al., "Germ-line transmission and expression of a human-derived yeast artificial chromosome," *Nature*, Mar. 18, 1993, 362(6417):255-258.

Jenkins N, Curling EM., "Glycosylation of recombinant proteins: problems and prospects", *Enzyme Microb Technol.* May 1994;16(5):354-64.

Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those from a mouse," *Nature*, May 29-Jun. 4, 1986, 321(6069):522-525.

Jones, "Analysis of polypeptides and proteins," *Adv. Drug Delivery Rev.*, Jan.-Apr. 1993, 10(1):29-90.

Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.

Kaneko et al., "Anti-inflammatory activity of immunoglobulin G resulting from Fc sialylation," *Science*, Aug. 4, 2006, 313(5787):670-673.

Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.

Kannagi et al., "Stage-specific embryonic antigens (SSEA-3 and -4) are epitopes of a unique globo-series ganglioside isolated from human teratocarcinoma cells," *EMBO J.*, 1983, 2(12):2355-2361.

Karlin S. et al., "Methods for assessing the statistical significance of molecular sequence features by using general scoring schemes", *Proc Natl Acad Sci U S A.* Mar. 1990;87(6):2264-8.

Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.

Kim et al., "Localization of the site of the murine IgG1 molecule that is involved in binding to the murine intestinal Fc receptor," *Eur. J. Immunol.*, 1994, 24:2429-2434.

Köhler et al., "Continuous cultures of fused cells secreting antibody of predefined specificity," *Nature*, Aug. 7, 1975, 256(5517):495-497.

Kontermann, "Intrabodies as therapeutic agents," *Methods*, Oct. 2004, 34(2):163-170.

Kostelny et al., "Formation of a bispecific antibody by the use of leucine zippers," *J. Immunol.*, Mar. 1, 1992, 148(5):1547-1553.

Kozbor, "A human hybrid myeloma for production of human monoclonal antibodies," *J. Immunol.*, Dec. 1984, 133(6):3001-3005.

Kriegler M et al., "A novel form of NF/cachectin is a cell surface cytotoxic transmembrane protein: ramifications for the complex physiology of TNF" *Cell.* Apr. 8, 1988;53(1):45-53.

Kudo et al., "Up-regulation of a set of glycosyltransferase genes in human colorectal cancer," *Lab. Invest.*, Jul. 1998, 78(7):797-811.

Lau et al., "N-Glycans in cancer progression," *Glycobiology*, Oct. 2008, 18(10):750-760.

Lee et al., "Bivalent antibody phage display mimics natural immunoglobulin," *J. Immunol. Methods*, Jan. 2004, 284(1-2):119-132.

Lee et al., "High-affinity human antibodies from phage-displayed synthetic Fab libraries with a single framework scaffold," *J. Mol. Biol.*, Jul. 23, 2004, 340(5):1073-1093.

Lefranc et al., "IMGT, the international ImMunoGeneTics database," *Nucleic Acids Res.*, Jan. 1, 1999, 27(1):209-212.

Lehninger, *Biochemistry: The Molecular Basis of Cell Structure and Function*, $2^{nd\ ed.}$, 1975, pp. 73-75, Worth Publishers, New York.

Leung et al., "A method for random mutagenesis of a defined DNA segment using a modified polymerase chain reaction," *Technique—A Journal of Methods in Cell and Molecular Biology*, Aug. 1989, 1(1):11-15.

Lindmark et al., "Binding of immunoglobulins to protein A and immunoglobulin levels in mammalian sera," *J. Immunol. Meth.*, Aug. 12, 1983, 62(1):1-13.

Liu C, et al., "Expansion of spleen myeloid suppressor cells represses NK cell cytotoxicity in tumor-bearing host" *Blood.* May 15, 2007;109(10):4336-42. Epub Jan. 23, 2007.

Liu et al., "Eradication of large colon tumor xenografts by targeted delivery of maytansinoids," *Proc. Natl., Acad. Sci. U.S.A.*, Aug. 6, 1996, 93(16):8618-8623.

LoBuglio et al., "Mouse/human chimeric monoclonal antibody in man: kinetics and immune response," *Proc. Natl. Acad. Sci. U.S.A.*, Jun. 1989, 86(11):4220-4224.

Lode et al., "Targeted therapy with a novel enediyene antibiotic calicheamicin $\Theta^1_1$ effectively suppresses growth and dissemination of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Louis et al., "The 2007 WHO classification of tumours of the central nervous system," *Acta. Neuropathol.*, Aug. 2007, 114(2):97-109.

Lu et al., "Single chain anti-c-Met antibody conjugated nanoparticles for in vivo tumor-targeted imaging and drug delivery," *Biomaterials*, Apr. 2011, 32(12):3265-3274.

(56) References Cited

OTHER PUBLICATIONS

MacFarlane GT, et al., "Formation of glycoprotein degrading enzymes by Bacteroides fragilis" *FEMS Microbiol Lett.* Jan. 15, 1991;61(2-3):289-93.

Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization Human antibodies from V-gene libraries displayed on phage," *J. Mol. Biol.*, Dec. 5, 1991, 222(3):581-597.

Marks et al., "By-passing immunization. Building high affinity human antibodies by chain shuffling," *Nature Biotechnology*, Jul. 1992, 10(7):779-783.

Mather et al., "Culture of testicular cells in hormone-supplemented serum-five medium," *Annals N.Y. Acad. Sci.*, 1982, 383 :44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

McKimm-Breschkin, J. et al., "Neuraminidase Sequence Analysis and Susceptibilities of Influenza Virus Clinical Isolates to Zanamivir and Oseltamivir," *Antimicrobial Agents and Chemotherapy*, vol. 47, No. 7, Jul. 2003, in 10 pages.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17):1850.

Mimura et al., "Role of oligosaccharide residues of IgG1-Fc in FcγRIIb binding," *J. Biol. Chem.*, Dec. 7, 2001, 276(49):45539-45547.

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.

Morelle, W. et al., "The Mass Spectrometric Analysis of Glycoproteins and their Glycan Sturctures", *Review in Current Analytical Chemistry*, vol. 1, No. 1 (2005), pp. 29-57.

Mori K, et al., "Non-fucosylated therapeutic antibodies: the next generation of therapeutic antibodies" *Cytotechnology*. Dec. 2007;55(2-3):109-14. Epub Oct. 31, 2007.

Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.

Morrison et al., "Chimeric human antibody molecules: mouse antigen-binding domains with human constant region domains," *Proc. Natl. Acad. Sci. U.S.A.*, Nov. 1984, 81(21):6851-6855.

Morrison, "Immunology. Success in specification," *Nature*, Apr. 28, 1994, 368(6474):812-813.

Munson et al., "Ligand a versatile computerized approach for characterization of ligand-binding systems," *Anal. Biochem.*, Sep. 1, 1980, 107(1):220-239.

Neuberger et al., "Recombinant antibodies possessing novel effector functions," *Nature*, Dec. 13-19, 1984, 312(5995):604-608.

Neuberger, "Generating high-avidity human Mabs in mice," *Nature Biotechnol.*, Jul. 1996, 14(7):826.

Nicolaou et al., "Calicheamicin $\Theta^1_1$: A rationally designed molecule with extremely potent and selective DNA cleaving properties and apoptosis inducing activity," *Angew. Chem. Intl. Ed. Engl.*, Feb. 1, 1994, 33(2):183-186.

Niculescu-Duvaz et al., "Antibody-directed enzyme prodrug therapy (ADEPT): A review," *Adv. Drg. Del. Rev.*, Jul. 7, 1997, 26(2-3):151-172.

Noto et al., "CD44 and SSEA-4 positive cells in an oral cancer cell line HSC-4 possess cancer stem-like cell characteristics," *Oral Oncol.*, Aug. 2013, 49(8):787-795.

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Papanastassiou et al., "The potential for efficacy of the modified (ICP 34.5') herpes simplex virus HSV1716 following intratumoural injection into human malignant glioma: a proof of principle study," *Gene Therapy*, Mar. 2002, 9(6):398-406.

Pearlman et al., *Peptide and Protein Drug Delivery, Chapter 6: Analysis of Protein Drugs*, Lee, ed., 1991, pp. 247-301, Marcel Dekker Publishing, New York.

Peipp et al., "Antibody fucosylation differentially impacts cytotoxicity mediated by NK and PMN effector cells," *Blood*, 2008, 112(6):2390-2399.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

Presta, "Antibody engineering," *Curr. Opin. Biotechnol.*, Aug. 1992, 3(4):394-398.

Presta, "Antibody engineering," *Curr. Opin. Struct. Biol.*, Aug. 1992, 2(4):593-596.

Proba et al., "Functional antibody single-chain fragments from the cytoplasm of *Escherichia coli*: influence of thioredoxin reductase (TrxB)," *Gene*, Jul. 4, 1995, 159(2):203-207.

Puigbò P, Guzmán E, Romeu A, Garcia-Vallvé S. OPTIMIZER: a web server for.optimizing the codon usage of DNA sequences. *Nucleic Acids Res*. Jul. 2007;35(Web Server issue):W126-31. Epub Apr. 16, 2007.

Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.

Ravetch et al., "Divergent roles for Fc receptors and complement in vivo," *Ann. Rev. Immunol.*, 1998, 16:421-432.

Ravetch et al., "Fc receptors," *Annu. Rev. Immunol.*, 1991, 9:457-492.

Reyes et al., "Expression of human β-interferon cDNA under the control of a thymidine kinase promoter from herpes simplex virus," *Nature*, Jun. 17, 1982, 297(5867):598-601.

(56) References Cited

OTHER PUBLICATIONS

Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):969-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol. Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science*. Jan. 9, 1987; 235(4785):177-82.
Smith RA et al., "The active form of tumor necrosis factor is a trimer" *J Biol Chem*. May 25, 1987;262(15):6951-4.
Smyth MJ, et al., "CD4+CD25+ T regulatory cells suppress NK cell-mediated immunotherapy of cancer" *J Immunol*. Feb. 1, 2006;176(3):1582-7.

Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2): 109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers Of Cytotoxic Agents In Cancer Therapy: A Review," in *Monoclonal Antibodies '84: Biological And Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tsai TI, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.
Tutt et al., "Trispecific F(ab')3 derivatives that use cooperative signaling via the TCR/CD3 complex and CD2 to activate and redirect resting cytotoxic T cells," *J. Immunol.*, Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem.* Jul. 5, 1989;264(19):11282-7.
Van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Vermeer AW et al., "The thermal stability of immunoglobulin: unfolding and aggregation of a multi-domain protein" *Biophys J.* Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.

(56) References Cited

OTHER PUBLICATIONS

Wikstrand et al., "Monoclonal antibody therapy of human gliomas: Current status and future approaches," *Cancer Metastasis Rev.*, 1999, 18(4):451-464.
Williams et al., "Cloning and sequencing of human immunoglobulin V lambda gene segments." *Eur. J. Immunol.*, Jul. 1993, 23(7):1456-1461.
Winter et al., "Making antibodies by phage display technology," *Annu. Rev. Immunol.*, 1994, 12:433-455.
Woof et al., "Human antibody-Fc receptor interactions illuminated by crystal structures," *Nat. Rev. Immunol.*, Feb. 2004, 4(2):89-99.
Yansura et al., "Nucleotide sequence selection for increased expression of heterologous genes in *Escherichia coli*," *Methods: A Companion to Methods in Enzymol.*, Aug. 1992, 4(2):151-158.
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yu et al., "Anti-GD2 antibody with GM-CSF, interleukin-2, and isotretinoin for neuroblastoma," *N. Engl. J. Med.*, Sep. 30, 2010, 363(14):1324-1334.
Zapata et al., "Engineering linear F(ab')$_2$ fragments for efficient production in *Escherichia coli* and enhanced antiproliferative activity," *Protein Eng.*, Oct. 1995, 8(10): 1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "Selection of tumor antigens as targets for immune attack using immunohistochemistry: I. Focus on gangliosides," *Int. J. Cancer*, Sep. 26, 1997, 73(1):42-49.

European Search Report issued in connection with corresponding European Patent Application No. 15181446.4, dated Dec. 7, 2015, 10 pages.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.
Piizi, G. and Hardinger, S., "Stereochemistry: an introduction," UCLA Chemistry 30A Presentation, Fall 2002, in 40 pages.
Solomons, G. and Fryhle, C., Chapter 5 titled, "Stereochemistry: Chiral Molecules," p. 184-228, in "Organic Chemistry," 7$^{th}$ Edition, Wiley, Jun. 18, 2001.
Lopes, J.F. et al., Simultaneous chromatographic separation of enantiomers, anomers and structural isomers of some biologically relevant monosaccharides. J. Chromatogr. A, (2008) 1188:34-42. Available online Dec. 15, 2007.
Demchenko, A.V., Ed.., Handbook of Chemical Glycosylation: Advances in Stereoselectivity and Therapeutic Relevance (2008) Wiley-VCH. Chapter 1. General Aspects of the Glycosidic Bond Formation, in 28 pages.

\* cited by examiner

| No. | Name | Associated disease |
|---|---|---|
| 1 | EF-Tu | Gastric cancer |
| 2 | Catalase | Gastric cancer |
| 3 | Heat shock protein 60 | Gastric cancer/Duodenal ulcer |
| 4 | FTSH (cell division protease) | Gastric cancer |
| 5 | DNAK (HSP 70) | Gastric cancer |
| 6 | CLPB (chaperone) | Gastric cancer |
| 7 | CAGA (immuniodominant antigen) | Gastric cancer |
| 8 | ATPase-alpha subunit | Gastric ulcer |
| 9 | UreB | Gastric ulcer |

ALKYNYL SUGAR ANALOGS FOR LABELING AND VISUALIZATION OF GLYCOCONJUGATES IN CELLS

CROSS REFERENCE TO RELATED APPLICATIONS

This application is a divisional of U.S. application Ser. No. 12/079,226 filed Mar. 24, 2008, titled "Alkynyl sugar analogs for the labeling and visualization of glycoconjugates in cells," and issued as U.S. Pat. No. 7,960,139 on Jun. 14, 2011, which claims priority to U.S. Provisional Patent Application Ser. No. 60/896,777, filed on Mar. 23, 2007, titled "Pro-alkynyl sugar analogs for the labeling and visualization of glycoconjugates in cells," the contents of which are incorporated in their entirety by reference as if fully disclosed herein.

STATEMENT REGARDING FEDERALLY SPONSORED RESEARCH OR DEVELOPMENT

This invention was made with Government support for research from the National Institutes of Health and The Skaggs Institute for Chemical Biology. The Government may have certain rights in the invention.

FIELD OF THE DISCLOSURE

The present disclosure provides a method for metabolic oligosaccharide engineering which uses azido and/or alkyne-bearing sugar analogs and/or precursors of fucose and sialic acid to incorporate azido and/or alkyne tags into cellular glycans that are fucosylated and sialylated. The derivatized glycan is labeled by a chemical probe comprising an azide group and a visualizable, isolatable, and/or fluorogenic group. The chemical probe binds covalently (labels) to alkynyl and/or azido groups displayed in cellular glycans via copper (I)-catalyzed [3+2] azide-alkyne cycloaddition (CuAAC) or click chemistry. The labeled glycans can be visualized at the cell surface, intracellularly, or in a cellular extract.

BACKGROUND OF THE INVENTION

Glycans are integral components of biological systems with far reaching activities, many of which are only beginning to be understood. Glycans constitute the most abundant and diverse class of biomolecules found in natural systems, consisting of oligosaccharide chains that are present as independent polysaccharides (e.g., cellulose, an important structural component in plants; and heparin sulfate, an import factor of blood clotting in mammals) or as glycoconjugates with lipids (glycolipids), proteins (glycoproteins, proteoglycans), and small molecule natural products (e.g., antibiotics such as erythromycin, vancomycin, and teicoplanin).

Glycans play a role in almost every aspect of cellular activity. Most glycans in higher eukaryotes are produced in the secretory pathway by glycosylation events, which entail the enzymatic transfer of saccharides or oligosaccharide chains onto lipids and proteins. Protein glycosylation is a complex co- or post-translational process that modifies the majority of the human proteome and serves a vast array of biological functions. Protein glycosylation exerts intrinsic effects on structure, from mediating folding and oligimerization, to increasing stability, solubility, and circulation time. Inside of the cell, glycans affect recognition, binding, targeting, and cellular distribution. At the cell surface, glycans are prominently displayed where they are involved in a host of molecular recognition events that modulate important physiological processes, such as cell-cell adhesion, inflammation, angiogenesis, coagulation, embryogenesis, differentiation, communication, and a myriad of other cellular signaling pathways.

Cell surface glycans have also been associated with physiological dysfunctions such as bacterial and viral infection, rheumatoid arthritis, and tumor progression. In the latter case, several types of oncofetal and aberrant glycans have been established to correlate with malignancy, invasiveness, inflammation and cancer metastasis. In particular, altered terminal fucosylation and sialylation, which are believed to result from changes in expression locations and levels of fucosyltransferases (an group of enzymes that transfers a fucose from a donor substrate to an acceptor substrate, a glycoconjugate or glycan) and sialyltransferases (a group of enzymes that transfers a sialic acid from a donor substrate to an acceptor substrate, a glycoconjugate or glycan) respectively, are associated with tumor malignancy. For example, glycan determinants like Lewis y, Lewis x, sialyl Lewis x, sialyl Lewis a, sialyl Tn, Globo H, fucosyl GM1, and polysialic acid are expressed at elevated levels in neoplastic tissues. For this reason, these epitopes are promising and eagerly pursued targets for glycan-based vaccines. Additionally, several congenital glycosylation disorders, lysosomal storage disorders, and immunological diseases have been linked with dysregulation of glycan catabolism/metabolism. Although known to be involved in physiological and pathophysiological events, the identification of many glycan structures and delineation of their mode of action at the molecular level has been complicated by their underpinning complexity.

Glycan complexity results from many factors. They are synthesized in a non-templated, post-translational process, which means that sites of glycoconjugate glycosylation and structures within them have proven, thus far, to be minimally predictable. This also means that glycans cannot be genetically manipulated in a similar fashion to DNA and proteins. Glycans are synthesized in the secretory pathway by a suite of enzymes that are subject to multifaceted controls. The end glycan products can have enormous structural complexity (many possible glycan structures, the diversity of which is also a function of the sugar building blocks), structural micro-heterogeneity (multiple different glycan structures attached to a glycoconjugate at the same position), and structural macro-heterogeneity (multiple sites and types of glycan attachment; for example, glycoproteins can be N-linked at Asn residues, or O-linked at Ser/Thr residues). Heterogeneity in glycan structures appears to be dynamically regulated and functionally significant, governing multivalent interactions on the cell surface. Heterogeneity and multivalency complicate structure-function studies and the isolation of homogenous glycans in meaningful amounts from natural sources is nearly impossible. For the procurement of homogenous glycoconjugates/glycans synthesis is the only viable route, but remains one of the most formidable challenges in glycobiology.

The link between glycan activity and complexity has presented major challenges to deciphering their activities on an individual protein, let alone, proteomic scale. Among the challenges facing global analysis are development of general methods for isolating glycans from complex proteomes; determining saccharide composition, site of protein modification, and fraction occupancy; and understanding the direct roles of glycans in cellular function and dysfunction.

Specific glycan-tagging systems provide a powerful method for probing the structure of heterogeneous glycans. The key to glycan tagging entails incorporating modified sugars derivatized with chemical reporting groups into cellular glycans (typically via the normal biosynthetic pathways, a process known as metabolic oligosaccharide engineering, or MOE) and then detecting the tagged-glycans by labeling their chemical reporting groups with a complementary probe that chemically reacts with them in a specific manner (a chemoselective manner). Many selective chemical probing techniques have been used for probing chemical reporting group-tagged glycoconjugates in cells. These methods include bioorthogonal reactions such as ketoneaminooxy/hydrazide ligation, Staudinger ligation, Michael addition, and the strain-promoted, and Cu(I)-catalyzed [3+2] azide-alkyne cycloaddition (CuAAC). Several chemical reporting groups are tolerated and successfully incorporated into glycoconjugates using MOE, including ketones, thiols, photoreactive groups, azides, and alkynes. These reporting sugars have been labeled with tags such as FLAG peptides, biotin, and fluorescent or fluorogenic molecules. The strength of these systems is that the labeled glycan products have the potential to be manipulated for specific glycan studies involving: enrichment and glycoproteomic analysis by means of mass spectrometry detection and/or quantitation by flow cytometry or visualization through microscopy to obtain information about glycan localization, trafficking, and dynamics.

The incorporation of exogenous natural or unnatural sugars into glycans has been achieved by cellular biosynthetic pathways. These processes involve multistep enzymatic transformations that render free sugars in the cytosol into nucleotide-donor sugars, the substrates for glycosyltransferases. In the case of fucose (Fuc), a salvage pathway consisting of Fuc kinase and GDP-Fuc (guanosine diphosphate fucose) pyrophosphorylase contributes to the production of GDP-Fuc, which is then exploited by fucosyltransferases (FucTs) located in the Golgi apparatus to add Fuc onto glycoconjugates. Modifications at the 6-position of Fuc are tolerated by the salvage pathway and FucTs. In the sialic acid (NeuAc) biosynthetic pathway, the precursor N-acetylmannosamine (ManNAc) is derived from GlcNAc or UDP-GlcNAc through specific epimerases, then sequentially converted to sialic acid (NeuAc) by the cytosolic enzymes ManNAc 6-kinase, sialic acid-9-phosphate synthase, and sialic acid-9-phosphate phosphatase. CMP-NeuAc is subsequently formed in the nucleus, and transported to the Golgi apparatus for glycan elaboration by sialyltransferases. Studies on metabolic delivery of N-acetyl mannosamine or ManNAc analogs show that N-acyl chains up to five carbon atoms long are tolerated by the sialic acid biosynthetic pathway.

Prior glycoprotein probes have limited utility due to issues of cellular toxicity. The incorporation of exogenous natural or unnatural sugars comprising non-toxic probes into glycans by cellular biosynthetic pathways is important to study aberrant glycosylation. Further understanding of the molecular details and correlations between altered glycosylation and pathological status is of great interest and is likely to provide useful information for diagnosis and disease prognosis, in addition to unveiling new therapeutic targets.

Glycosylation is the process of glycoconjugate synthesis and is an important bioinformational process that occurs co- or posttranslationally on greater than 50% of eukaryotic proteins. In living organisms, it affects protein bioactivity and metabolic turnover. Inside of cells, it mediates protein folding, stability, and trafficking. At the cell surface, glycans participate in molecular recognition events that are central to biological and pathological processes like cell-cell interactions involved in adhesion, migration, and metastasis; host-pathogen interactions critical for bacterial and viral infections; and, initiation of immune response.

Aberrant glycosylation is often observed in pathological conditions such as inflammation and cancer metastasis. In particular, altered terminal fucosylation and sialylation, which are believed to result from changes in expression locations and levels of fucosyltransferases and sialyltransferases, are associated with tumor malignancy. For example, glycan determinants like Lewis y, Lewis x, sialyl Lewis x, sialyl Lewis a, sialyl Tn, Globo H, fucosyl GM1, and polysialic acid are expressed at elevated levels in neoplastic tissues. For this reason, these epitopes are promising and eagerly pursued targets for glycan-based vaccines. However, cellular glycans are complex, heterogeneous populations, resulting from a non-template-driven process that cannot be manipulated genetically. This complexity makes the isolation and identification of glycans for structural analysis one of the most challenging and defining tasks in glycobiology.

Specific glycan-tagging systems provide a powerful method for probing the structure of heterogeneous glycans. The key to glycoconjugate tagging entails incorporating derivatized sugar chemical reporting groups into cellular glycoconjugates (typically via the normal biosynthetic pathways, a process known as metabolic oligosaccharide engineering, or MOE), and then detecting the tagged glycoconjugates by labeling their chemical reporting groups with a complementary probe that chemically reacts with them in a specific manner. Many selective chemical probing techniques have been used for performing chemistry with chemical reporting group-tagged glycoconjugates in cells. These methods include bioorthogonal reactions such as ketoneaminooxy/hydrazide ligation, Staudinger ligation, Michael addition, and the strain-promoted and Cu(I)-catalyzed [3+2] azide-alkyne cycloaddition.

Several chemical reporting groups are tolerated and successfully incorporated into glycoconjugates using MOE, including ketones, thiols, photoreactive groups, azides, and alkynes. These reporting sugars have been labeled with tags, such as FLAG peptides, biotin, and fluorescent or fluorogenic molecules. The strength of these systems is that the labeled glycan products have the potential to be manipulated for specific glycan studies involving: enrichment and glycoproteomic analysis by mass spectrometry; detection and/or quantitation by flow cytometry; or visualization through microscopy to obtain information about glycan localization, trafficking, and dynamics.

The incorporation of exogenous natural or unnatural sugars into glycoconjugates is achieved by cellular biosynthetic pathways. These processes involve multistep enzymatic transformations that render free sugars in the cytosol into nucleotide-donor sugars, the substrates for glycosyltransferases. In the case of fucose (Fuc), a salvage pathway consisting of Fuc kinase and GDP-Fuc pyrophosphorylase contributes to the production of GDP-Fuc, which is then exploited by fucosyltransferases (FucTs) located in the Golgi apparatus to add Fuc onto glycoconjugates. Previous work has shown that modifications at the 6-position of Fuc are tolerated by the salvage pathway and FucTs. In the sialic acid (NeuAc) biosynthetic pathway, the precursor N-acetylmannosamine (ManNAc) is derived from N-acetylglucosamine (GlcNAc) or uridine diphosphate GlcNAc (UDP-GlcNAc) through specific epimerases, then sequentially converted to sialic acid by the cytosolic enzymes ManNAc 6-kinase, sialic acid-9-phosphate synthase, and sialic acid- 9-phosphate phosphatase. Cytosine monophosphate NeuAc (CMP-NeuAc) is subsequently formed in the nucleus, and transported to the Golgi apparatus for glycan elaboration by sialyltransferases. Studies on metabolic delivery of Man-NAc or its analogs show that N-acyl chains up to five carbon atoms long are tolerated by the sialic acid biosynthetic pathway.

Currently available glycoconjugate probes can be of limited utility due to potential cellular toxicity. The incorporation of exogenous natural or unnatural sugars comprising non-toxic probes into glycoconjugates by cellular biosynthetic pathways is important to study aberrant glycosylation which is often observed in pathological conditions such as inflammation and cancer metastasis. Further understanding of the molecular details and correlations between altered glycosylation and pathological status is of great interest and is likely to provide useful information for diagnosis and disease prognosis, in addition to unveiling new therapeutic targets.

SUMMARY OF THE INVENTION

In one exemplary implementation, a method is disclosed comprising presenting an alkynyl-derivatized sugar to a cell, wherein the alkynyl-derivatized sugar has an alkynyl functional group, and wherein the cell is capable of producing a glycoconjugate; incorporating the alkynyl-derivatized sugar into the cell, wherein the alkynyl-derivatized sugar is subsequently used by the cell to produce a tagged glycoconjugate; wherein the tagged glycoconjugate includes: a glycan portion; a conjugate portion; and an alkynyl functional group; and reacting the tagged glycoconjugate with a probe to produce a labeled, tagged glycoconjugate.

In another exemplary implementation, the labeled glycoconjugate is detected to determine the location of the labeled glycoconjugate in the cell.

In another exemplary implementation, the labeled glycoconjugate is detected to determine the quantity of the labeled glycoconjugate in the cell.

In another exemplary implementation, the labeled glycoconjugate is detected to determine the identity of the labeled glycoconjugate in the cell.

In another exemplary implementation, the alkynyl-derivatized sugar is an alkynyl-derivatized fucose.

In another exemplary implementation, the alkynyl-derivatized sugar is an alkynyl-derivatized fucose derivative.

In another exemplary implementation, the alkynyl-derivatized sugar is 1,2,3,4-tetraacetyl alkynyl fucose or a 1,2,3,4-tetraacetyl alkynyl fucose derivative.

In another exemplary implementation, the alkynyl-derivatized sugar is an alkynyl-derivatized N-acetylmannosine or an alkynyl-derivatized N-acetylmannosine derivative.

In another exemplary implementation, the alkynyl-derivatized sugar is a sialic acid precursor.

In another exemplary implementation, the alkynyl-derivatized sugar is 1,3,4,6-tetra-O-acetyl-N-4-pentynoylmannosamine.

In another exemplary implementation, the alkynyl-derivatized sugar is peracetylated.

In another exemplary implementation, the alkynyl-derivatized sugar is acetylated.

In another exemplary implementation, the alkynyl-derivatized sugar is ManNAcyne.

In another exemplary implementation, the alkynyl-derivatized sugar is NeuAcyne.

In another exemplary implementation, the alkynyl-derivatized sugar is Fucyne.

In another exemplary implementation, the alkynyl-derivatized sugar is bioorthogonal.

In another exemplary implementation, the alkynyl-derivatized sugar is subsequently incorporated into a glycoconjugate at a terminal position.

In another exemplary implementation, the alkynyl-derivatized sugar is subsequently incorporated into a glycoprotein.

In another exemplary implementation, the alkynyl-derivatized sugar is subsequently incorporated into a glycoprotein at a terminal position.

In another exemplary implementation, the alkynyl-derivatized sugar is subsequently incorporated into a glycolipid.

In another exemplary implementation, the alkynyl-derivatized sugar is subsequently incorporated into a glycolipid at a terminal position.

In another exemplary implementation, the alkynyl-derivatized sugar is capable of fluorescence.

In another exemplary implementation, the alkynyl-tagged glycoconjugate is a fucosylated glycoconjugate.

In another exemplary implementation, the alkynyl-tagged glycoconjugate is a sialylated glycoconjugate.

In another exemplary implementation, the probe is azido-derivatized.

In another exemplary implementation, the probe reacts with the alkynyl-tagged glycoconjugate by azide-alkyne cycloaddition.

In another exemplary implementation, the azide-alkyne cycloaddition reaction is copper (I) catalyzed.

In another exemplary implementation, the probe-tagged glycoconjugate reaction generates a triazole moiety.

In another exemplary implementation, the triazole moiety is generated while maintaining bioorthogonality of the functional groups.

In another exemplary implementation, the triazole moiety is generated at biological pH.

In another exemplary implementation, the triazole moiety is generated with nearly 100% reaction efficiency.

In another exemplary implementation, the probe is fluorogenic and becomes fluorescent upon azide-alkyne cycloaddition reaction with the tagged glycoconjugate.

In another exemplary implementation, the probe additionally comprises a biotin group.

In another exemplary implementation, the probe additionally comprises a coumarin group.

In another exemplary implementation, the coumarin probe is 3-azido-7-hydroxycoumarin.

In another exemplary implementation, the detecting step comprises visualizing the location of labeled glycoconjugates by one or more techniques of flow cytometry and confocal microscopy.

In another exemplary implementation, the detecting step comprises quantifying the labeled glycoconjugates by one or more techniques of flow cytometry, SDS-PAGE, Western blot, ELISA, confocal microscopy, and mass spectroscopy.

In another exemplary implementation, the detecting step comprises identifying the labeled glycoconjugates by one or more techniques of flow cytometry, SDS-PAGE, Western blot, ELISA and confocal microscopy.

In another exemplary implementation, the incorporating step further comprises growing the cell in the presence of from about 1 to about 1000 micromolar concentration of the alkynyl-derivatized fucose.

In another exemplary implementation, the incorporating step comprises growing the cell in the presence of from about 50 to about 400 micromolar concentration of the alkynyl-derivatized fucose.

In another exemplary implementation, the incorporating step comprises growing the cell in the presence of from about 1 to about 100 micromolar concentration of the alkynyl-derivatized N-acetylmannosamine.

In another exemplary implementation, the incorporating step comprises growing the cell in the presence of from about 5 to about 50 micromolar concentration of the alkynyl-derivatized N-acetylmannosamine.

In another exemplary implementation, the labeled glycoconjugate in the cell is on the surface of the cell.

In another exemplary implementation, the cells are permeabilized prior to labeling.

In another exemplary implementation, a method is disclosed comprising presenting an alkynyl-derivatized sugar to a cell, wherein the alkynyl-derivatized sugar has an alkynyl functional group, and wherein the cell is capable of producing a glycoconjugate; incorporating the alkynyl-derivatized sugar into the cell, wherein the alkynyl-derivatized sugar is subsequently used by the cell to produce a tagged glycoconjugate; wherein the tagged glycoconjugate includes a glycan portion; a conjugate portion; and an alkynyl functional group; and reacting the tagged glycoconjugate with a probe to produce a labeled, tagged glycoconjugate; wherein the resultant toxicity of the method is improved by at least 10% as compared to presenting an azido-derivatized sugar to produce the tagged glycoconjugate.

In another exemplary implementation, the resultant toxicity is improved by at least 50%.

In another exemplary implementation, a compound is disclosed comprising: an alkynyl tagged glycoconjugate; and an azido-derivatized probe; wherein the alkynyl tagged glycoconjugate and azido-derivatized probe are joined via a triazole moiety.

In another exemplary implementation, the compound is fluorogenic.

In another exemplary implementation, the resultant toxicity measured when the compound is presented to a cell or cells is increased by no more than 10% as compared to the toxicity measured in a cell or cells to which no compound is presented.

In another exemplary implementation, the azido-derivatized probe further comprises a biotin-labeled moiety.

In another exemplary implementation, the azido-derivatized probe further comprises an antibody-labeled moiety.

In another exemplary implementation, an alkynyl-derivatized fucose is formed by the process of: obtaining L-(+)-galactonic acid γ-lactone; transforming, L-(+)-galactonic acid γ-lactone to 1,2:3,4-Di-O-isopropylidene-α-L-galactose by treatment with Amberlite IR120 and NaBH$_4$; transforming the hydroxyl group at position 6 of 1,2:3,4-Di-O-isopropylidene-α-L-galactose to an alkynyl group by Seyferth-Gilbert homologation, or specifically first by treatment with PCC and NaOAc; filtering this mixture through a bed of silica gel, and then treating the filtrate with a suspension of tBuOK and (EtO)$_2$P(O)CHN$_2$, thus creating 6,7-deoxy-1,2:3,4-di-O-isopropylidene-α-L-galacto-hept-6-ynopyranoside, referred to as 6-alkynylfucose diacetonide, or the diisopropylidene-Fuc intermediate; removing the diacetonide protecting groups from 6-alkynylfucose diacetonide to form 6-alkynyl fucose; and acetylating the resultant deprotected product 6-alkynyl fucose to form 1,2,3,4-tetraacetyl alkynyl fucose, as a mixture of pyranoside and furanoside forms.

In another exemplary implementation, an azido-derivatized fucose is prepared by the process of: obtaining 1-(+)-galactonic acid γ-lactone; transforming L(+)-galactonic acid γ-lactone to 1,2:3,4-Di-O-isopropylidene-α-L-galactose by treatment with Amberlite IR120 and NaBH$_4$; transforming the hydroxyl group at position 6 of 1,2:3,4-Di-O-isopropylidene-α-L-galactose to an azido group by treatment with TsCl and NaN$_3$ to create 6,7-deoxy-1,2:3,4-di-O-isopropylidene-α-L-Fucose-6-azide, referred to as 6-azidofucose diacetonide, or the diisopropylidene-Fuc intermediate; removing the diacetonide protecting groups from 6-alkynyl-fucose diacetonide to form 6-alkynyl fucose; and acetylating the resultant deprotected product 6-alkynyl fucose to form 1,2,3,4-tetraacetyl alkynyl fucose, as a mixture of pyranoside and furanoside forms.

In another exemplary implementation, an alkynyl-tagged glycoconjugate is made by the process of fucosylating a glycoconjugate with the 1,2,3,4-tetraacetyl alkynyl fucose by endogenous cellular metabolic pathways for glycan synthesis.

In another exemplary implementation, a compound is made by the steps of fucosylating a glycoconjugate with the 1,2,3,4-tetraacetyl alkynyl fucose by endogenous cellular metabolic pathways for glycan synthesis; and coupling the azido-derivatized probe with the fucosylated glycoconjugate at least partially comprised of 1,2,3,4-tetraacetyl alkynyl fucose via cycloaddition.

In another exemplary implementation, an alkynyl ManNAc-tagged glycoconjugate is made by the process of: obtaining D-mannoside hydrochloride; reacting the D-mannoside hydrochloride with N-succinimidyl 4-pentynoate to yield alkynyl ManNAc derivative; acetylating the alkynyl ManNAc derivative; and sialylating a glycoconjugate with the acetylated alkynyl ManAc derivative.

In another exemplary implementation, a fluorescent glycoconjugate is made by the process of: obtaining D-mannoside hydrochloride; reacting the D-mannoside hydrochloride with N-succinimidyl 4-pentynoate to yield alkynyl ManNAc derivative; acetylating the alkynyl ManNAc derivative; sialylating a glycoconjugate with the acetylated alkynyl ManNAc derivative; and coupling an azido-derivatized probe with the sialylated glycoconjugate at least partially comprised of the acetylated alkynyl ManNAc derivative via cycloaddition.

In another exemplary implementation, A method is disclosed comprising the steps of: presenting an alkynyl-derivatized sugar to a cell, wherein the alkynyl-derivatized sugar has an alkynyl functional group, and wherein the cell is capable of producing a glycoconjugate; incorporating the alkynyl-derivatized sugar into the cell, wherein the alkynyl-derivatized sugar is subsequently used by the cell to produce a tagged glycoconjugate; wherein the tagged glycoconjugate includes a glycan portion; a conjugate portion; and an alkynyl functional group; reacting the tagged glycoconjugate with a probe to produce a labeled, tagged glycoconjugate; detecting the labeled glycoconjugate; and differentially analyzing the proteomes of the cells incorporating detected, labeled glycoconjugate.

In another exemplary implementation, the cells are *H. pylori* or *H. pylori*-infected cells.

In another exemplary implementation, a method is disclosed comprising the steps of: providing an alkynyl-derivatized sugar to a cell population, wherein the alkynyl-derivatized sugar has an alkynyl functional group, and wherein the cells are capable of producing a glycoconjugate; incorporating the alkynyl-derivatized sugar into the cell, wherein the alkynyl-derivatized sugar is subsequently used by the cells to produce a tagged glycoconjugate, wherein the tagged glycoconjugate includes a glycan portion; a conjugate portion; and an alkynyl functional group; reacting the tagged glycoconjugate with a probe to produce a labeled, tagged glycoconjugate; visualizing the labeled, tagged glycoconjugate population of the cells; and differentially analyzing the subset of cells expressing labeled, tagged Lewis antigen epitopes.

In another exemplary implementation, a method is disclosed comprising generating antibodies to the subset of cells expressing Lewis antigen epitopes.

In another exemplary implementation, cells are presented with derivatized sugars for a limited period of time.

In another exemplary implementation, the limited period of time is 30 minutes.

In another exemplary implementation, derivatized sugars are presented to a cell for a limited time, and the presenting step is succeeded by presenting the cell with non-derivatized sugars.

In another exemplary implementation, derivatized sugars are presented to a cell for a limited time, and both preceded and succeeded by presenting the cell with non-derivatized sugars.

In another exemplary implementation, derivatized sugars are subsequently labeled and detected at various time intervals subsequent to the limited presentment of such sugars to the cell.

In another exemplary implementation, various time interval detections of derivatized sugars are compared so as to assess cellular trafficking of glycoconjugates.

In another exemplary implementation, differential cellular trafficking of glycoconjugates is assessed.

In another exemplary implementation, various time interval detections of derivatized sugars are compared with various interval detections of the location of various intracellular and extracellular bodies (e.g. nucleus, Golgi apparatus, lysosome) so as to assess differential cellular trafficking of glycoconjugates.

In another exemplary implementation, derivatized sugars that are presented to a cell for a limited time are alkynyl-derivatized sugars.

In another exemplary implementation, derivatized sugars that are presented to a cell for a limited time are azido-derivatized sugars.

In another exemplary implementation, derivatized sugars that are presented to a cell for a limited time are both alkynyl and azido-derivatized sugars.

In another exemplary implementation, derivatized sugars that are presented to a cell for a limited time are incorporated into fucosylated glycoconjugates.

In another exemplary implementation, derivatized sugars that are presented to a cell for a limited time are incorporated into sialylated glycoconjugates.

In another exemplary implementation, derivatized sugars that are presented to a cell for a limited time and are preceded and succeeded by presenting the cell with non-derivatized sugars are incorporated into both fucosylated and sialylated glycoconjugates.

BRIEF DESCRIPTION OF THE FIGURES

The patent or application contains at least one drawing executed in color. Copies of this patent or patent application publication with color drawings will be provided by the Office upon request and payment of the necessary fee.

FIG. 1 (D) shows cell growth analysis after treatment with different derivatized sugar Fuc analogs: alkynyl Fuc 1, azido Fuc 2, control 3, and untreated. Jurkat cells were grown in the presence of 200 micromolar each Fuc analog for 3 days before cell numbers were counted. The data represent the percentage of treated cells vs. untreated cells (n=4).

FIG. 2 shows analysis of cell surface labeling of sialyl glycoconjugates.

cells treated with control Fuc 3; open histograms: cells treated with alkynyl-derivatized Fuc 1. Mean fluorescence intensity (MFI) of each peak is indicated.

Figure 9A:
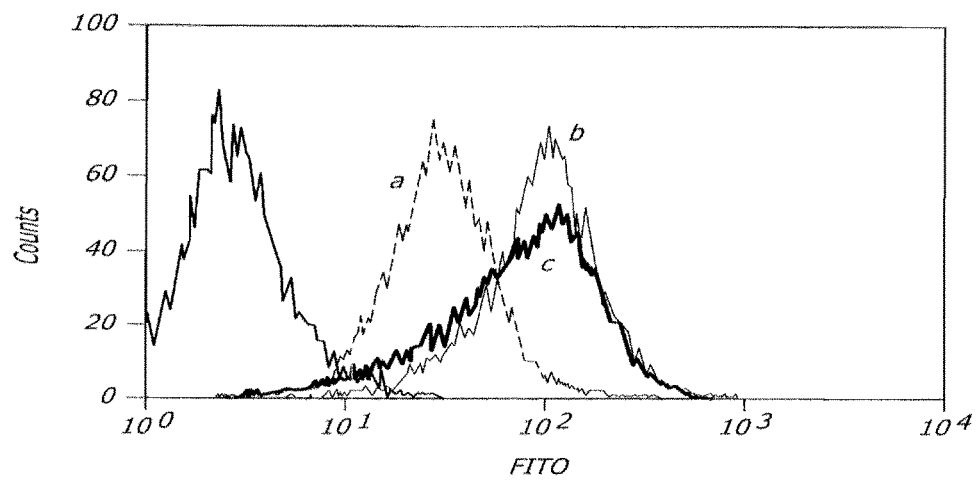
Figure 9B:
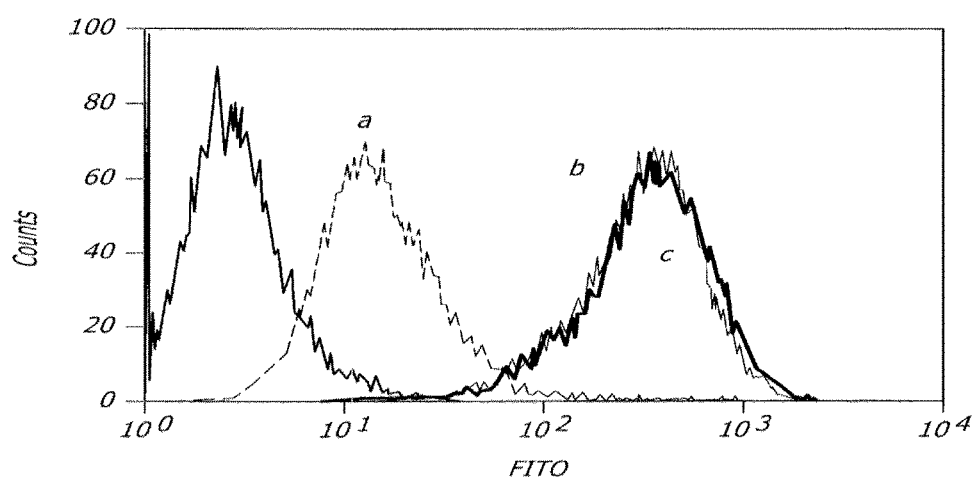

FIG. 9 shows lectin staining of alkynyl-derivatized Fuc 1-tagged PC-3 prostate cancer cells. Cells were treated with 200 micromolar derivatized alkynyl-derivatized Fuc 1, or Fuc 3, or left untreated. After three days, cells were labeled with biotin-conjugated AAL/fluorescein-conjugated streptavidin (A) or fluorescein-conjugated UEA-I (B). Fluorescent signal was detected by flow cytometry. AAL was used to detect α-1,6- or α-1,3-linked Fuc; UEA-I was used to detect α-1,2-linked Fuc. Filled histogram: untreated cells without lectin stain; open histogram c: untreated cells stained with lectin; open histogram b: control Fuc 3-treated cells stained with lectin; open histogram a: alkynyl-derivatized Fuc 1-treated cells stained with lectin. AAL, Aleuria Aurantia Lectin; UEA-1, Ulex Europaeus Agglutinin I.

Figure 10A:
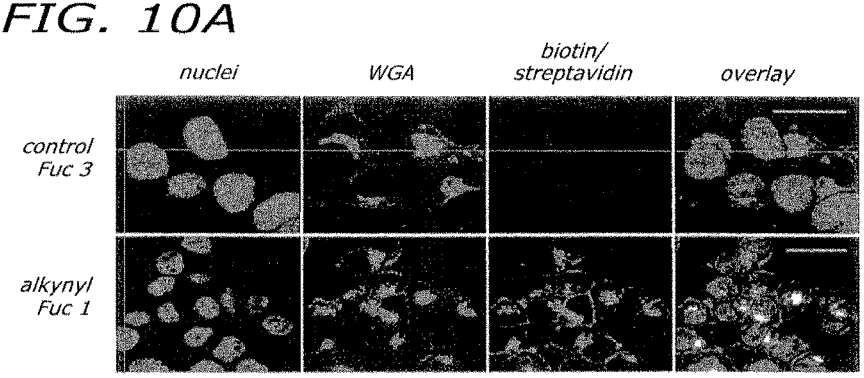
Figure 10B:
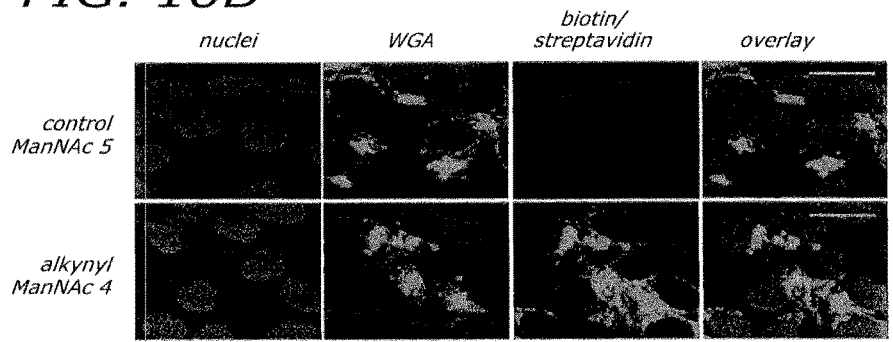

FIG. 10 shows fluorescent imaging of fucosyl and sialyl glycoconjugates in cells. Confocal microscopy of MCF-7 breast cancer cells treated with 200 micromolar derivatized Fuc analogs (A) or 25 micromolar derivatized ManNAc analogs (B). Cells were biotin-labeled and stained with streptavidin (fluorescein; green), WGA lectin (Alexa Fluor 594; red), and Hoechst 33342 (blue). Scale bars represent 20 micrometers.

Figure 11:
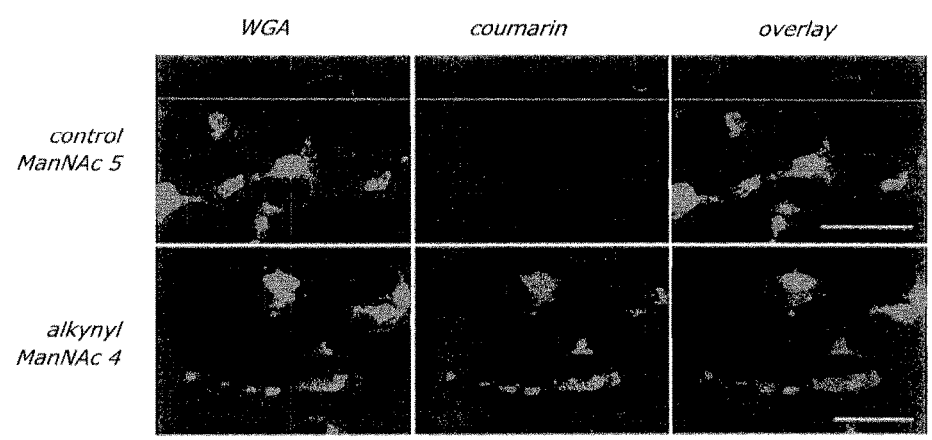

FIG. 11 shows visualization of tagged sialyl glycoconjugates in cells using labeling via click-activated probe 7: confocal microscopy of coumarin-labeled MCF-7 cells. Cells were treated with 25 micromolar ManNAc analogs 5 or 4, and then labeled with fluorogenic coumarin probe 7 (blue) and stained with WGA lectin (Alexa Fluor 594; red). Scale bars represent 20 micrometers.

Figure 12:
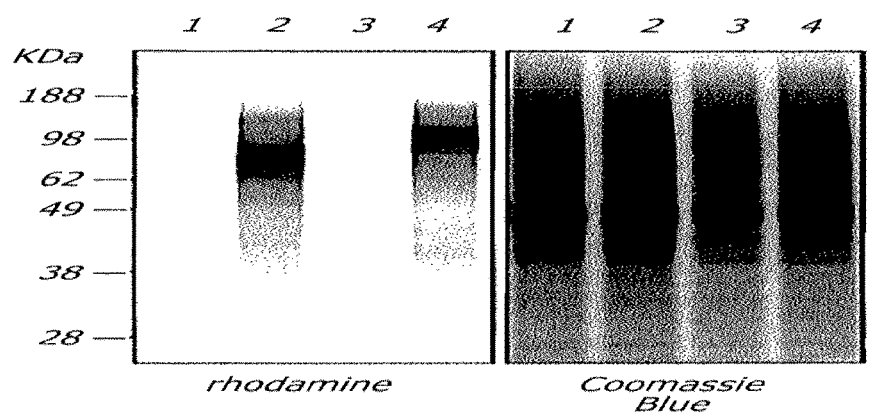

FIG. 12 shows detection of alkynyl-tagged glycoconjugates in cell extracts. Glycoconjugates tagged with alkynyl-derivatized sugars were labeled and detected by azido rhodamine probe. Protein extracts from cells grown with different sugars were analyzed by SDS-PAGE (12% gel), fluorescent imaging, and Coomassie Blue stain (lane 1: control Fuc 3; lane 2: alkynyl Fuc 1; lane 3: control ManNAc 5; lane 4: alkynyl ManNAc 4).

FIG. 13 shows SDS-gel based derivatized fucosylated glycoproteomic profiling of *H. pylori*. (A) Affinity purification of derivatized alkynyl-tagged fucosylated proteins in various *H. pylori* strains after labeling with biotin probe. HS: gastric strain. HU: gastric ulcer strain. HD: duodenal ulcer strain. HC: gastric cancer strain. (B) Protein identified from different strains of *H. pylori* by tagging with derivatized alkynyl Fuc and further labeling and subsequent visualization and isolation of tagged glycoconjugates.

Figure 14:
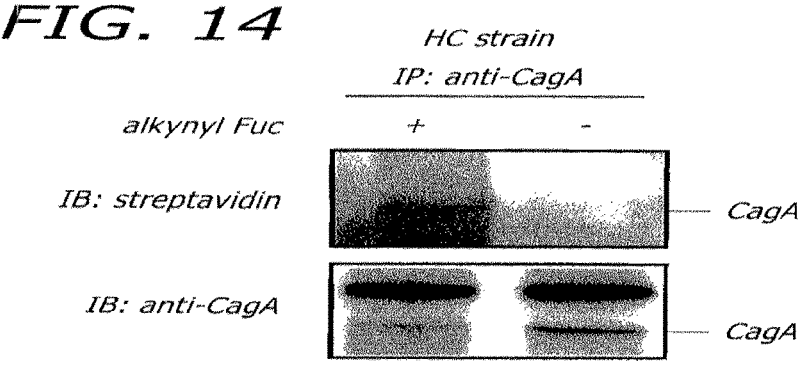

FIG. 14 shows examination of derivatized alkynyl-tagged fucosylated glycoconjugates on CagA in *H. pylori* cancer strain by immunoprecipitation and immunoblotting.

Figure 15:
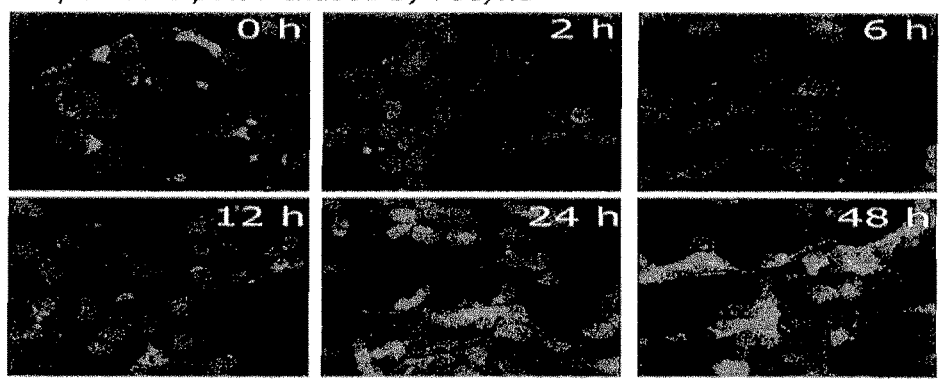

FIG. 15 shows time-lapse microscopy of pulse-chased Hep3b cells grown for 30 minutes in medium containing Fucyne, with tagged glycoconjugate structures subsequently labeled with biotin and detected using streptavidin-FITC as a secondary label at 2 hour intervals after completion of the Fucyne pulse. Additional cellular structures are visualized using alternative labeling systems (e.g., WGA lectin used to visualize Golgi apparatus, and Hoechst used to visualize nucleus).

DETAILED DESCRIPTION OF THE INVENTION

As used herein, the term "abnormal" means an organism whose proteome differs in identity (whether measure by individual or total protein identity), relative ratio, and/or glycosylation status of measurable cellular proteins.

As used herein, the term "alkynyl group" or "alkyne functional group" means an alkyne functional group (also called acetylene functional group), which is a hydrocarbon comprised of a triple bond between two carbon atoms.

As used herein, the term "alkynyl-derivatized sugar" means a synthetic sugar analog, in pro-molecular, metabolic precursor, and/or downstream metabolite form, substituted with an alkynyl group.

As used herein, the term "alkynyl-derivatized" means a molecule in which at least one carbon is substituted with an alkynyl functional group.

As used herein, the term "alkynyl functional group" means a chemical moiety consisting of at least one triple bond between two carbon atoms, with the formula $C_nH_{2n-2}$.

As used herein, the term "alkynyl-tagged", means a glycoconjugate incorporating an alkynyl-derivatized sugar.

As used herein, the terms "alkynyl fucose," "alkynyl Fuc" and "Fucyne" are used interchangeably.

As used herein, the term "alkynyl N-acetylmannosamine," "alkynyl ManNAc" and "ManNAcyne" are used interchangeably.

As used herein, the term "alkynyl sialic acid," "alkynyl NeuAc" and "NeuAcyne" are used interchangeably.

As used herein, the term "antibody" means proteins that are found in blood or other bodily fluids of vertebrates, and are used by the immune system to identify and neutralize foreign objects, such as bacteria and viruses.

As used herein, the term "azido-derivatized" means a molecule in which at least one carbon is substituted with an azido functional group.

Amino acid residues in peptides shall hereinafter be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to Proteins: Structure and Molecular Properties by Creighton, T. E., W. H. Freeman & Co., New York 1983.

As used herein, the term "bioorthogonal" means chemical reactants and reactions that are compatible with living systems. Bioorthogonal reactions proceed in high yield under physiological conditions and result in covalent bonds between reactants that are otherwise stable in these settings.

As used herein, the term "bioorthogonal chemical reporting group" means a non-native, non-perturbing, inert chemical functional group, which can be modified in biological systems by chemo-selective reactions with exogenously delivered probes.

As used herein, the term "binding moiety" means a moiety or functional group capable of binding to a second chemical entity.

As used herein, the term "cellular glycan" or "cell glycan" refers to a glycan (either alone or as part of a glycoconjugate) that may be at the cell surface, intracellular, or within a cell lysate.

As used herein, the term "capable of producing" means that a cell is able to perform the designated biochemical function via a known or unknown biosynthetic pathway; for example, many cells are able to produce glycosylated proteins through the FucT salvage pathway.

As used herein, the term "capturing" means chemically linking a molecule of interest with a physical support, wherein the molecule of interest is immobilized.

As used herein, the term "chemoselective" means the preferential reaction of a chemical reagent with only one out of two or more different available functional groups.

As used herein, the term "coumarin" means any of a group of fluorogenic compounds related to benzopyrone or 2-chromenone that are capable of fluorescence modulation dependent on position of substitution and identity of functional groups.

As used herein, the term "conjugate portion" means a non-sugar portion of a glycoconjugate.

As used herein, the term "click-activated" means any reaction that bioorthogonally proceeds in a manner that changes the chemical and/or physical properties of the resultant molecule.

As used herein, the term "cycloaddition" means a chemical cyclization reaction, in which two π bonds are lost and two σ bonds are gained—the reaction can proceed catalyzed or uncatalyzed or in a concerted or stepwise manner.

As used herein, the term "differential modification of +1 Da" means an amino acid that may bear a chemical modification resulting in a molecular weight shift of 1 dalton (Da). For example, a Asn residue with a N-linked bond to a glycan can be hydrolyzed to Asp, resulting in a +1 Da change in molecular weight. A differential modification is added to searching algorithms for MS peptide sequencing when all residues of a particular amino acid are not modified (e.g., only Asn residues formerly covalently bound to a glycan will have the +1 Da differential modification). Searching with a diff mod determines if and where a shift from the Asn residue to an Asp residue has occurred, and therefore assigns formerly N-glycosylated sites.

As used herein, the term "derivatization" is used to describe a technique used in chemistry which transforms a chemical compound into a product of similar chemical structure, called a derivative. For example, when reference is made to a sugar analog or precursor that has been "derivatized" with an alkyne group, it is meant that the sugar analog is bearing an alkynyl group.

As used herein, the term "determining" means measuring (qualitatively or quantitatively) a chemical or physical characteristic of a sample of interest.

As used herein, the term "differential analysis" means assessment of relative quantities and identities of proteomes as compared among heterogeneous samples or organisms.

As used herein, the term "epitope" means the part of a macromolecule that is recognized by the immune system, specifically by antibodies, B cells, or T cells.

As used herein, the term "flow cytometry" or "FACS" means a technique for examining the physical and chemical properties of particles or cells suspended in a stream of fluid, through optical and electronic detection devices.

As used herein, the term "fluorescent labeled" means derivatizing a molecule with a fluorescent material.

As used herein, the term "fluorogenic" or "fluorescent reporting group" means a material capable of supporting a chemical reaction dependent on the presence of a particular analyte material. Said analyte-dependent chemical reaction produces a fluorescent reporting molecule.

As used herein, the term "fluorescent" means a material exhibiting fluorescence.

As used herein, the term "fucose" is interchangeable with its abbreviation (Fuc) and means a six-carbon deoxy pyran sugar, distinguished from other hexoses by a L-configuration and an unsubstituted carbon at the 6-position.

As used herein, the term "fucosyltransferase (FucT)" means an enzyme that transfers a fucose from a donor substrate, GDP-fucose (GDP=Guanosine diphosphate), to an acceptor substrate, a glycoconjugate or glycan.

As used herein, the term "fucosylated" means a molecule (typically a glycoconjugate or glycan) that has been covalently appended with a Fuc residue (typically by a FucT).

As used herein, the term "functional group" (or "moiety") means a specific group of atoms within molecules that are responsible for the characteristic chemical reactions of those molecules. The same functional group will undergo the same or similar chemical reaction(s) regardless of the size of the molecule it is a part of. However, its relative reactivity can be modified by nearby functional groups.

As used herein, the term "GDP analog" means a molecular derivative of Guanosine diphosphate (GDP).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans are typically comprised of monosaccharides linked together with O-glycosidic bonds. For example, cellulose is a glycan (or more specifically a glucan) composed of β-1,4-linked D-glucose, and chitin is a glycan composed of β-1,4-linked N-acetyl-D-glucosamine Glycans can be homo or heteropolymers of monosaccharide residues, and can be linear or branched. Glycans can be found attached to lipids and proteins, as in glycoproteins and proteoglycans. They are generally found on the exterior surface of cells. O- and N-linked glycans are very common in eukaryotes but may also be found, although less commonly, in prokaryotes. N-linked glycans are attached through amide bonds to asparagine residues found in the N-glycosylation consensus sequon. The sequon is a Asn-X-Ser or Asn-X-Thr sequence, where X is any amino acid except proline. O-linked glycans are attached through glycosidic bonds with oxygen groups on serine and threonine residues in proteins, or hydroxyl groups of lipids and small molecules.

As used herein, the term "glycoconjugate" means a molecule covalently modified with glycans.

As used herein, the term "glycoprotein" means a protein covalently modified with glycan(s). There are four types of glycoproteins: 1) N-linked glycoproteins, 2) O-linked glycoproteins (mucins), 3) glucosaminoglycans (GAGs, which are also commonly called proteoglycans), 4) GPI-anchored. Most glycoproteins have structural micro-heterogeneity (multiple different glycan structures attached within the same glycosylation site), and structural macro-heterogeneity (multiple sites and types of glycan attachment).

As used herein, the term "glycoproteomics" refers to a branch of proteomics that identifies, catalogs, and characterizes proteins containing carbohydrates as a post-translational modification. Glycoproteomics also refers to the study of a cell, tissue, or organism's glycan and glycoprotein content at any point in time.

As used herein, the term "glycosylation" means the enzymatic transfer of saccharides or oligosaccharide chains onto glycoconjugates. Protein glycosylation is a complex co- or post-translational process that modifies the majority of the human proteome, vastly expanding its functional repertoire.

As used herein, the term "harvesting" means concentrating, collecting, purifying and/or storing a material of interest.

As used herein, the term "isolated" means glycoconjugates that can be selectively separated by secondary detection means.

As used herein, the term "incorporating" means introducing a compound or derivative of a compound into the intracellular environment by any method, including but not limited to inclusion in media or restricted media; electroporation; injection; phagocytosis; active transport; endocytosis; active transport; passive transport; carrier-assisted transport; vesicle-mediated transport; and diffusion.

As used herein, the term "labeled glycoprotein" means a glycoprotein covalently attached via cycloaddition to a moiety that can facilitate the manipulation of the "labeled glycoprotein," such as the isolation, visualization, detection, and quantification of the labeled glycoprotein.

As used herein, the term "liquid chromatography-mass spectrometry" or "LC-MS" refers to an analytical chemistry technique that combines the physical separation capabilities of liquid chromatography (aka HPLC) with the mass analysis capabilities of mass spectrometry (MS). LC-MS is a powerful technique used for many applications which has very high sensitivity and specificity. Generally its application is oriented towards the specific detection and potential identification of chemicals in the presence of other chemicals (in a complex mixture). LC-MS is also used in the study of proteomics where components of a complex mixture must be detected and identified in some manner. The bottom-up proteomics LC-MS approach to proteomics generally involves protease digestion (usually Trypsin) followed by LC-MS with peptide mass fingerprinting or LC-MS$^2$ (tandem MS) to derive the sequence of individual peptides.

As used herein, the term "metabolic oligosaccharide engineering" or "MOE" means the process of incorporating an alkynyl-derivatized sugar into a glycoconjugate.

As used herein, the term "MudPIT" or Multidimentional Protein Identification Technology refers to the characterization of protein mixtures using tandem LC-MS$^2$. A peptide mixture that results from digestion of a protein mixture is fractionated by multiple steps of liquid chromatography. The eluent from the chromatography stage can be either directly introduced to the tandem MS through electrospray ionization, or laid down on a series of small spots for later mass analysis using MALDI.

As used herein, the term "proteome" refers to the entire complement of proteins expressed by a genome, cell, tissue or organism. More specifically, it is the expressed proteins at a given time point under defined conditions.

As used herein, the term "presenting" means introducing into the extracellular environment, including, but not limited to, inclusion in growth media, restricted media, reaction solution, buffer, and/or staining solution.

As used herein, the term "proteomics" refers to the study of the proteome. Proteomics has largely been practiced through the separation of proteins by two dimensional gel electrophoresis. In the first dimension, the proteins are separated by isoelectric focusing, which resolves proteins on the basis of charge. In the second dimension, proteins are separated by molecular weight using SDS-PAGE. The gel is dyed with Coomassie Blue or silver stain to visualize the proteins. Spots on the gel are proteins that have migrated to specific locations. The mass spectrometer has augmented proteomics. Peptide mass fingerprinting identifies a protein by cleaving it into short peptides and then deduces the protein's identity by matching the observed peptide masses against a sequence database. Tandem mass spectrometry, on the other hand, can get sequence information from individual peptides by isolating them, colliding them with a non-reactive gas, and then cataloging the fragment ions produced.

As used herein, the term "pulse-chase" means a method for examining a cellular process occurring over time by successively exposing the cells to a labeled compound (pulse) and then to the same compound in nonlabeled form (chase).

As used herein, the term "reacting" means inducing a chemical reaction between two or more substances, including, but not limited to, catalyzing such reaction and providing appropriate supporting reaction substituents to maintain biochemical pH and thermodynamic environments.

As used herein, the term "reporting group" means a molecule that has properties capable of presenting detectable feedback about events transpiring in a test system (from a controlled in vitro assay to a complex biological system).

As used herein, the term "sialylated" means a molecule (typically a glycoconjugate or glycan) that has been covalently appended with a sialic acid (NeuAc) residue (typically by a sialyl transferase)

As used herein, the term "tagged" means a glycoconjugate that has incorporated an alkynyl-derivatized sugar through any permissive biosynthetic pathway involved in glycoconjugate synthesis.

As used herein, the term "toxicity" means the relative percentage of cells (assayed by any method of cell counting) surviving 3 days in vitro or in vivo after addition of sugar analogs (natural and/or derivatized) compound to the relevant cellular environment.

As used herein, the term "trafficking" means the movement of material from one location to another within, into, or out of a cell, and any associated modifications of the material occurring in the process.

In one exemplary implementation, the disclosure provides a method of labeling glycoconjugates in a cell, the method comprising: presenting an alkynyl-derivatized sugar; incorporating the alkynyl-derivatized sugar into glycoconjugates in the cell by growing the cell in the presence of the alkynyl-derivatized sugar to create an tagged glycoconjugate (alkynyl-tagged glycoconjugate); contacting the tagged glycoconjugate with a chemical probe wherein said chemical probe reacts with said alkynyl group in the tagged glycoconjugate to create a labeled, tagged glycoconjugate; and manipulating the labeled, tagged glycoconjugate for further analysis. Analysis can include detecting labeled alkynyl-derivatized-tagged glycoconjugates through fluorescence to determine one or more of the location and relative abundance; or isolating them to determine their identity and relative abundance.

In one exemplary implementation, the disclosure provides a method of labeling fucosylated glycoconjugates in a cell, the method comprising: presenting an alkynyl-derivatized fucose; tagging a glycoconjugate in the cell by growing the cell in the presence of an alkynyl-derivatized fucose to create an alkynyl-tagged fucosylated glycoconjugate; labeling the alkynyl-tagged glycoconjugate with a chemical probe which will bind covalently to the alkynyl group to create a labeled-glycoconjugate; and detecting the labeled, tagged glycoconjugate to determine that the labeled-glycoconjugate in the cell is a fucosylated glycoconjugate.

In another exemplary implementation, the disclosure provides a method of identifying a sialylated glycoconjugate in a cell, the method comprising: presenting an alkynyl-derivatized N-acetylmannosamine; tagging a glycoconjugate in the cell by growing the cell in the presence of alkynyl-derivatized N-acetylmannosamine to create a tagged, sialylated alkynyl-derivatized glycoconjugate; labeling the alkynyl-derivatized glycoconjugate with a chemical probe which will bind covalently to the alkynyl group to create a labeled, tagged glycoconjugate; and detecting the labeled-glycoconjugate to determine that the labeled-glycoconjugate in the cell is a sialylated glycoconjugate.

In a further exemplary implementation, the disclosure provides a method of incorporating an alkynyl derivatized sugar into a glycoconjugate in a cell, the method comprising: presenting an alkynyl-derivatized sugar; and tagging a glycoconjugate in the cell by growing the cell in the presence of the alkynyl-derivatized sugar to create an labeled, tagged glycoconjugate.

In one exemplary implementation, the alkynyl-derivatized sugar tagged glycoconjugate is a fucosylated glycoconjugate and the alkynyl-derivatized sugar is an alkynyl-derivatized fucose. In a specific exemplary implementation, the alkynyl-derivatized fucose is 1,2,3,4-tetraacetyl alkynyl fucose.

In another exemplary implementation, the tagged glycoconjugate is a sialylated-glycoconjugate and the alkynyl-derivatized sugar is an alkynyl-derivatized N-acetylmannosamine. In a specific exemplary implementation, the alkynyl-derivatized N-acetylmannosamine is 1,3,4,6-tetra-O-acetyl-N-4-pentynoylmannosamine.

In another exemplary implementation, the disclosure provides a method of detecting an alkynyl-tagged glycoconjugate, the method comprising: contacting the alkynyl-derivatized sugar tagged glycoconjugate with a chemical probe wherein said chemical probe reacts with said alkynyl group in the alkynyl-derivatized sugar-tagged glycoconjugate to create a labeled, tagged glycoconjugate; and detecting the labeled, tagged glycoconjugate to determine one or more of the location and the abundance of the labeled-glycoconjugate in the cell. In one exemplary implementation, the contacting step is performed on a cell surface, on a permeabilized cell, or on a cellular extract.

In one exemplary implementation, the disclosure provides a method of metabolic oligosaccharide engineering (MOE) that incorporates derivatized alkyne-bearing sugar analogs into cellular glycoconjugates, thereby creating alkynyl-tagged glycoconjugates.

In one exemplary implementation, the alkyne-derivatized sugar analogs utilized in MOE are minimally toxic to the cell.

In one exemplary implementation, the alkyne-derivatized sugar analogs utilized in MOE minimally alter the cell's normal proteosome glycosylation pattern.

In one exemplary implementation, the derivatized alkynyl sugars are peracetylated.

In one exemplary implementation, the derivatized alkynyl sugars are acetylated.

In one exemplary implementation, the derivatized alkynyl sugars are derivatized fucose (Fuc).

In one exemplary implementation, the derivatized alkynyl sugars are fucose analog precursors capable of subsequent intracellular derivatization and subsequent incorporation into cellular, cell surface and/or extracellular fucosylated glycoconjugates.

In one exemplary implementation, the derivatized alkynyl sugars are sialic acid precursors capable of subsequent derivatization and incorporation into cellular, cell surface and/or extracellular sialylated glycoconjugates.

In one exemplary implementation, the derivatized alkynyl sugars are ManNAcyne.

In one exemplary implementation, the derivatized alkynyl sugars are NeuACyne.

In one exemplary implementation, the derivatized alkynyl sugars are Fucyne.

In one exemplary implementation, the derivatized alkynyl sugars are metabolic precursors to derivatized fucose and sialic acid analogues capable of subsequent intracellular metabolic incorporation into fucosylated and/or sialylated glycoconjugates.

In one exemplary implementation, the derivatized alkynyl sugars are capable of metabolic incorporation into fucosylated and/or sialylated glycoconjugates where they are subsequently capable of azido-alkynyl cycloaddition covalent binding with an azido-derivatized probe so as to create a labeled, tagged glycoconjugate.

In one exemplary implementation, the derivatized alkynyl sugars are bioorthogonal.

In one exemplary implementation, derivatized alkynyl sugars are incorporated into glycoconjugates.

In one exemplary implementation, derivatized alkynyl sugars are incorporated into glycoconjugates at the terminal position.

In one exemplary implementation, derivatized alkynyl sugars are incorporated into fucosylated glycoconjugates.

In one exemplary implementation, derivatized alkynyl sugars are incorporated into sialylated glycoconjugates.

In one exemplary implementation, derivatized alkynyl sugars capable of fluorescence by further derivatization are incorporated into glycoconjugates.

In one exemplary implementation, derivatized alkynyl sugars are incorporated into glycoproteins.

In one exemplary implementation, derivatized alkynyl sugars are incorporated into glycolipids.

In one exemplary implementation, the glycoconjugate is a fucosylated glycoconjugate or a sialylated glycoconjugate.

In another exemplary implementation, the glycoconjugate is a fucosylated glycoconjugate and the alkynyl-derivatized sugar originates from an alkynyl-derivatized fucose in the cell by MOE. In a specific exemplary implementation, the alkynyl-derivatized fucose is 1,2,3,4-tetraacetyl alkynyl fucose.

In one exemplary implementation, the alkynyl-tagged glycoconjugate is a sialylated-glycoconjugate and the alkynyl-derivatized sugar originates from alkynyl-derivatized N-acetylmannosamine in the cell by MOE.

In a specific exemplary implementation, the alkynyl-derivatized N-acetylmannosamine is 1,3,4,6-tetra-O-acetyl-N-4-pentynoylmannosamine.

In another exemplary implementation, the MOE sugar incorporating step further comprises growing the cell in the presence of the alkynyl-derivatized fucose, from about 1 to about 1000 micromolar concentrations in the growth medium.

In another exemplary implementation, the MOE sugar incorporating step comprises growing the cell in the presence of the alkynyl-derivatized N-acetylmannosamine, from about 1 to about 100 micromolar concentration in the growth medium.

In one exemplary implementation, the labeled-glycoconjugate is a cellular glycoconjugate located on the surface of the cell. In another exemplary implementation, the method further comprises treating the cell to permeabilize the cell prior to the contacting step.

In another exemplary implementation, azide bearing probes additionally comprising one or more of biotin and coumarin groups are bound covalently to alkynyl-tagged glycoconjugates to provide labeled glycoconjugates.

In one exemplary implementation, tagged glycoconjugates are capable of subsequent chemoselective labeling.

In one exemplary implementation, tagged glycoconjugates are labeled with a probe by azide-alkyne cycloaddition.

In one exemplary implementation, the probe is fluorogenic.

In one exemplary implementation, tagged glycoconjugates are labeled with a probe by CuAAC.

In one exemplary implementation, tagged glycoconjugates are labeled with a probe by azide-alkyne cycloaddition so as to generate a triazole moiety at the tagged glycoconjugate-probe interface.

In one exemplary implementation, tagged glycoconjugates are labeled with a probe by azide-alkyne cycloaddition so as to generate a triazole moiety at the tagged glycoconjugate-probe interface in aqueous solutions.

In one exemplary implementation, tagged glycoconjugates are labeled with a probe by azide-alkyne cycloaddition so as to generate a triazole moiety at the tagged glycoconjugate-probe interface at biologically relevant pH.

In one exemplary implementation, tagged glycoconjugates are labeled with a probe by azide-alkyne cycloaddition so as to generate a triazole moiety at the tagged glycoconjugate-probe interface while maintaining bioorthogonality of the reaction components and products.

In one exemplary implementation, tagged glycoconjugates are labeled with a probe by azide-alkyne cycloaddition so as to generate a triazole moiety at the tagged glycoconjugate-probe interface at biological pH.

In one exemplary implementation, tagged glycoconjugates are labeled with a probe by azide-alkyne cycloaddition so as to generate a triazole moiety at the tagged glycoconjugate-probe interface with nearly quantitiative reaction efficiency.

In one exemplary implementation, the probe is an azido-derivatized probe.

In one exemplary implementation, the probe is a coumarin.

In one exemplary implementation, the probe is biotin.

In one exemplary implementation, the probe additionally includes an secondary binding label.

In one exemplary implementation, the probe is additionally capable of being isolated or quantified directly.

In one exemplary implementation, the probe is additionally capable of being isolated or quantified indirectly through use of secondary binding/detection means.

In one exemplary implementation, the probe is additionally capable of being isolated or quantified through use of antibody-antigen interactions.

In one exemplary implementation, the probe is additionally capable of being isolated or quantified through use of lectin-glycan interactions.

In one exemplary implementation, the probe is additionally capable of being isolated or quantified through use of streptavidin/avidin-biotin binding.

In one exemplary implementation, the probe is additionally capable of being isolated or quantified through use of a fluorophore.

In a further exemplary implementation, a variety of techniques are disclosed for visualization of the labeled cellular glycoconjugate.

In one exemplary implementation, labeled, tagged glycoconjugates are visualized on the cell surface of a eukaryotic or prokaryotic cell.

In one exemplary implementation, labeled, tagged glycoconjugates are isolated.

In one exemplary implementation, labeled, tagged glycoconjugates are visualized.

In one exemplary implementation, labeled, tagged glycoconjugates are isolated through streptavidin/avidin-biotin interactions.

In one exemplary implementation, labeled, tagged glycoconjugates are isolated through antibody-antigen interactions.

In one exemplary implementation, labeled, tagged glycoconjugates are visualized through azide-alkyne cycloaddition-mediated fluorescence.

In one exemplary implementation, labeled, tagged glycoconjugates are quantified through azide-alkyne cycloaddition-mediated fluorescence.

In one exemplary implementation, the chemical probe comprises an azide group. In a specific exemplary implementation, the chemical probe binds covalently to the alkynyl group in tagged-glycoconjugates by CuAAC, thereby creating labeled-glycans.

In one exemplary implementation, the chemical probe further comprises one of a visualizable probe and a fluorogenic probe. In one exemplary implementation, the visualizable probe comprises a biotin group. In another exemplary implementation, the fluorogenic probe comprises a coumarin group.

In one exemplary implementation, the detecting step comprises visualizing the labeled glycoconjugate by one or more techniques of flow cytometry, SDS-PAGE, Western blot, ELISA, confocal microscopy, and mass spectrometry. In another exemplary implementation, the detecting step further comprises quantifying the labeled-glycoconjugate by one or more techniques of flow cytometry, SDS-PAGE, Western blot, ELISA and confocal microscopy.

In one exemplary implementation, derivatized sugars are presented to a cell for a limited time, and succeeded by presenting the cell with non-derivatized sugars.

In one exemplary implementation, derivatized sugars are presented to a cell for a limited time, and both preceded and succeeded by presenting the cell with non-derivatized sugars.

In one exemplary implementation, the derivatized sugars are subsequently labeled and detected at various time intervals subsequent to the limited presentment of such sugars to the cell.

In one exemplary implementation, the various time interval detections of derivatized sugars are compared so as to assess cellular trafficking of glycoconjugates.

In one exemplary implementation, the various time interval detections of derivatized sugars are compared so as to assess differential cellular trafficking of glycoconjugates.

In one exemplary implementation, the various time interval detections of derivatized sugars are compared with various interval detections of the location of various intracellular and extracellular bodies (e.g. nucleus, Golgi apparatus, lysosome) so as to assess differential cellular trafficking of glycoconjugates.

In one exemplary implementation, derivatized sugars are presented to a cell for a limited time are alkynyl-derivatized sugars.

In one exemplary implementation, the derivatized sugars presented to a cell for a limited time are alkynyl-derivatized sugars.

In one exemplary implementation, the derivatized sugars presented to a cell for a limited time are azido-derivatized sugars.

In one exemplary implementation, the derivatized sugars presented to a cell for a limited time are both alkynyl and azido-derivatized sugars.

In one exemplary implementation, the derivatized sugars presented to a cell for a limited time are incorporated into fucosylated glycoconjugates.

In one exemplary implementation, the derivatized sugars presented to a cell for a limited time, preceded and succeeded by presenting the cell with non-derivatized sugars are incorporated into sialylated glycoconjugates.

In one exemplary implementation, the derivatized sugars presented to a cell for a limited time, preceded and succeeded by presenting the cell with non-derivatized sugars are incorporated into both fucosylated and sialylated glycoconjugates.

In one exemplary implementation, the derivatized sugars presented to a cell for a limited time, preceded and succeeded by presenting the cell with non-derivatized sugars are presented to the cells with CuAAC catalysts.

In one exemplary implementation, the derivatized sugars presented to a cell for a limited time, preceded and succeeded by presenting the cell with non-derivatized sugars are presented to the cells without CuAAC catalysts.

Herein disclosed, alkynyl Fuc and alkynyl ManNAc analogs are synthesized and utilized as reporting saccharides in a method to tag fucosylated and sialylated glycoconjugates in mammalian cells. Previously, a fluorescent labeling technique for probing metabolically labeled fucosylated glycoconjugates in cells was reported by this laboratory.

In the previous approach, derivatized azido Fuc analogs incorporated into glycoconjugates were labeled with a 1,8-naphthalimide fluorogenic probe, by using Cu(I)-catalyzed azide-alkyne [3+2] cycloaddition, or alkyne-azide "click" reaction. The click-activated fluorescent labeling was used for specifically utilizing azido-derivatized labels to label alkynyl-derivatized, sugar-tagged fucosylated and sialylated glycoconjugates, and is also effective for use in so-called "pulse-chase" applications where there is limited presentment of the azido-derivatized sugar to the cell, and/or the presentment of the azido-derivatized sugar to the cell is in low concentration. In the present method, alkynyl Fuc and alkynyl ManNAc analogs show reduced toxicity to cells when compared with azido Fuc analogs. Moreover, when these alkynyl derivatized sugars are coupled with biotin, click-activated fluorogenic coumarin, and other fluorescent probes, this method allows for the isolation of fucosylated and sialylated glycoconjugates for further analysis, and fluorescent imaging (where alkynyl sugar labeling causes less background signal). This method can be used for visualizing glycan dynamics inside of cells and to identify important glycan markers.

Synthesis of Alkynyl Sugars and Biotinylated Azide Probe.

In one exemplary implementation of the disclosure, an Intermediary of Alkynyl Derivatized Fucose is 1,2:3,4-Di-O-isopropylidene-α-L-galactose, 17. To L-galactono-1,4-lactone (10 g, 56.1 mmol) in MeOH (60 mL) and water (250 mL) at 0° C. was added Amberlite IR 120 (H$^+$) resin (50 mL). NaBH$_4$ (2.2 g, 56.1 mmol) was added portionwise, and the reaction mixture was stirred for 1 h at room temperature. The resin was removed by filtration, and the filtrate was evaporated. The residue was dissolved in acetone (220 mL), CuSO$_4$ (22.2 g, 0.14 mol) and H$_2$SO$_4$ (1 mL) was added and the solution was stirred at room temperature overnight. The CuSO$_4$ was removed by filtration, and the filtrate was neutralized with Ca(OH)$_2$. After removal of Ca(OH)$_2$ and concentration, the residue was purified by flash column chromatography on silica gel (AcOEt/hexane 1:1) to afford 17 (9.1 g, 62%).

In one exemplary implementation of the disclosure, peracetylated alkynyl derivatives of Fuc 1 and ManNAc 4, shown in Scheme 1, are synthesized and used to tag fucosylated and sialylated glycoconjugates, respectively, in vivo. The sugar derivatives are synthesized in their peracetylated forms, as this modification is known to increase their cellular uptake efficiency. The acetate esters are subsequently hydrolyzed in the cytosol.

Scheme 1. Modified sugar analogs and probes

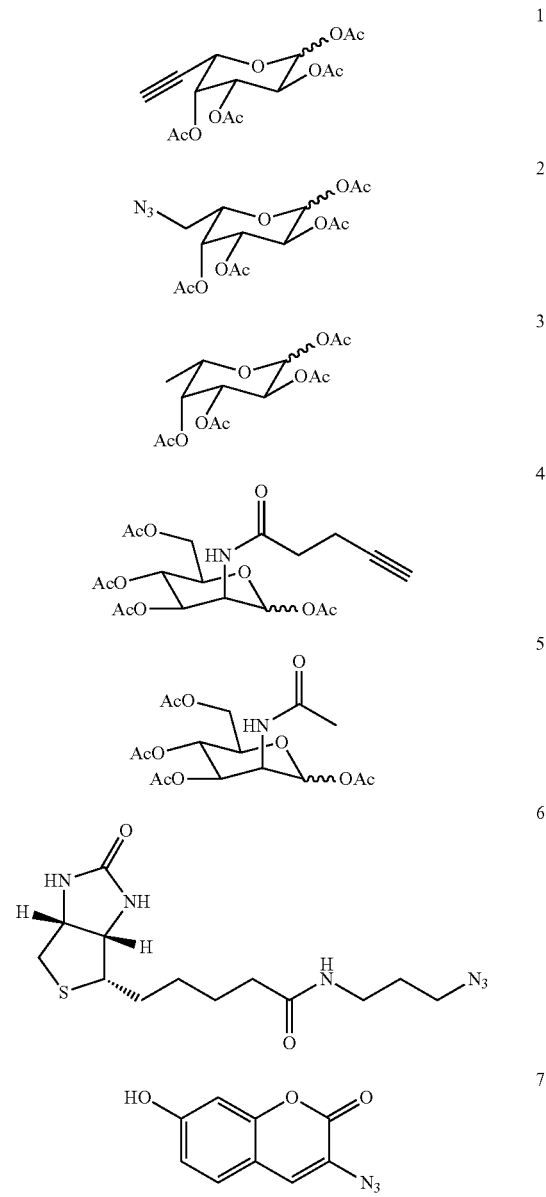

In one aspect of the disclosure, the synthesis of alkynyl Fuc (1, see Example 1, Scheme 2) proceeds from a known four-step transformation, beginning with L(+)-galactonic acid γ-lactone and ending with the alkynyl diisopropylidene-Fuc intermediate. Subsequent protecting group removal followed by acetylation of the intermediate yields the desired compound 1, as a mixture of pyranoside and furanoside forms. This mixture is used directly for labeling fucosylated glycoconjugates in cells.

Scheme 2

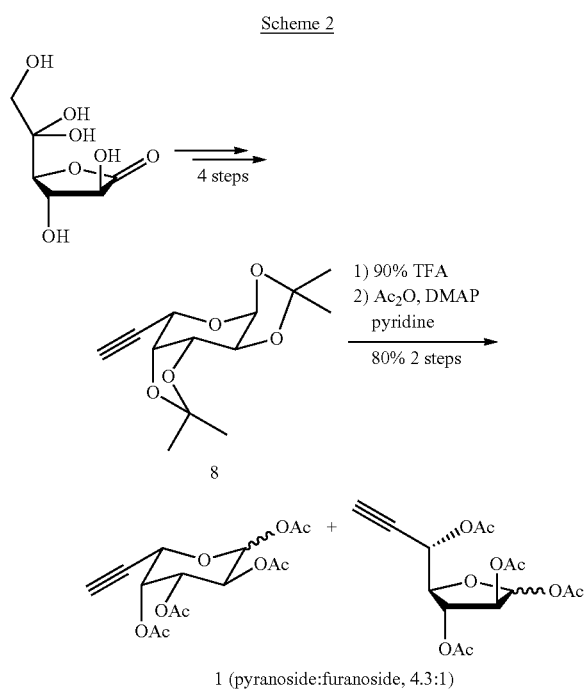

1 (pyranoside:furanoside, 4.3:1)

In another aspect of the disclosure, compound 4 is synthesized and used for tagging sialylated glycoconjugates. D-Mannosamine hydrochloride is reacted with N-succinimidyl 4-pentynoate in triethylamine to yield alkynyl ManNAc derivative (see Example 2, Scheme 3). The alkynyl ManNAc 4 is subsequently obtained by acetylation.

Scheme 3

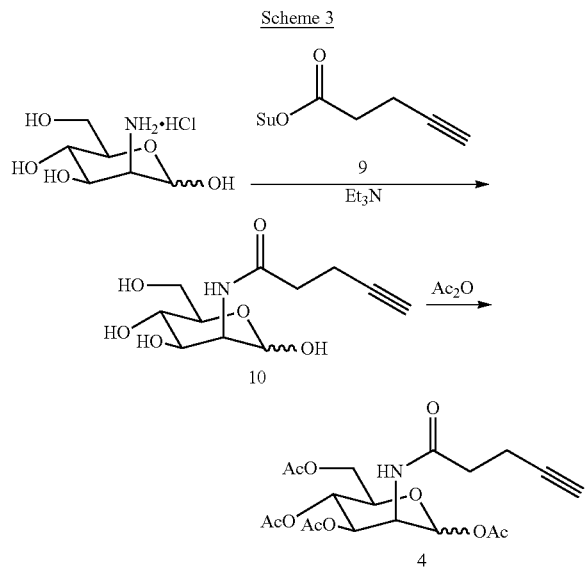

The coupling partner, biotinylated azido probe 6, is synthesized by coupling of biotin to 1-azido-3-aminopropane (see Example 4, Scheme 4). Fluorogenic probe 7, 3-azido-7-hydroxycoumarin, is synthesized as reported. Modified sugar analogs and probes used in this study are illustrated in Scheme 1.

Scheme 4

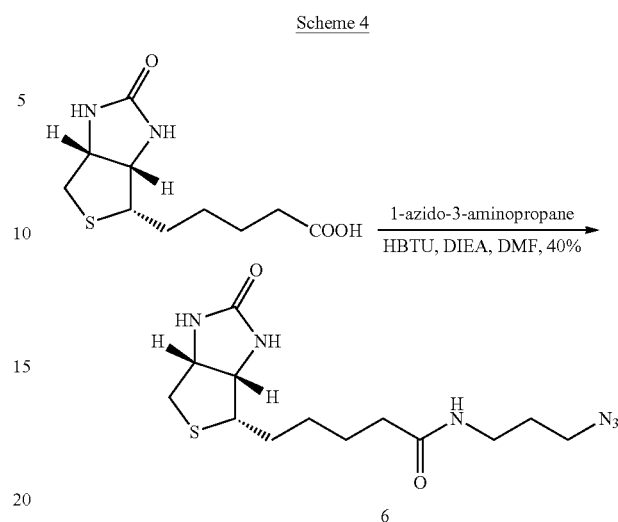

Fluorescent Labeling of Alkynyl Glycoconjugates at the Cell Surface.

In another exemplary implementation, a method for labeling fucosylated glycoconjugates at the cell surface is disclosed. In one aspect, Jurkat cells are grown in the presence of derivatized alkynyl Fuc 1. After treatment, cells are subjected to CuAAC (click chemistry) to couple biotinylated azido probe 6 with any alkynyl Fuc-bearing glycoconjugates, and stained with fluorescein-conjugated streptavidin.

Labeling alkynyl Fuc-bearing cell surface glycoconjugates is illustrated in FIG. 1. FIG. 1 shows analysis of cells tagged with Fuc analogs analyzed by monitoring fluorescence intensity with flow cytometry after labeling with a biotin azide probe 6 and staining cells with fluorescein-conjugated streptavidin. As shown in FIG. 1A, the derivatized alkynyl Fuc 1-treated cells show increased fluorescence intensity compared with control Fuc 3-treated cells, as analyzed by flow cytometry. This indicates that alkynyl-derivatized Fuc residues are incorporated into ("tag") cell surface glycoconjugates and that these tags can serve as binding sites for chemoselective cycloaddition labeling. Without being bound by theory, incorporation of the derivatized Fuc analogs into fucosylated glycoconjugates likely occurs via the Fuc salvage pathway. Alkynyl Fuc analog 1-treated cells showed a dose dependent increase of fluorescence signal, with a 3-fold greater mean fluorescence intensity (MFI) compared with Fuc treated cells at 200 micromolar concentration (FIG. 1B). The data also showed saturation of alkynyl Fuc 1 incorporation within one-day of incubation, although there was a slight increase of labeling signal on cells treated for three days with alkynyl Fuc 1 (FIG. 1C).

Figure 1A:
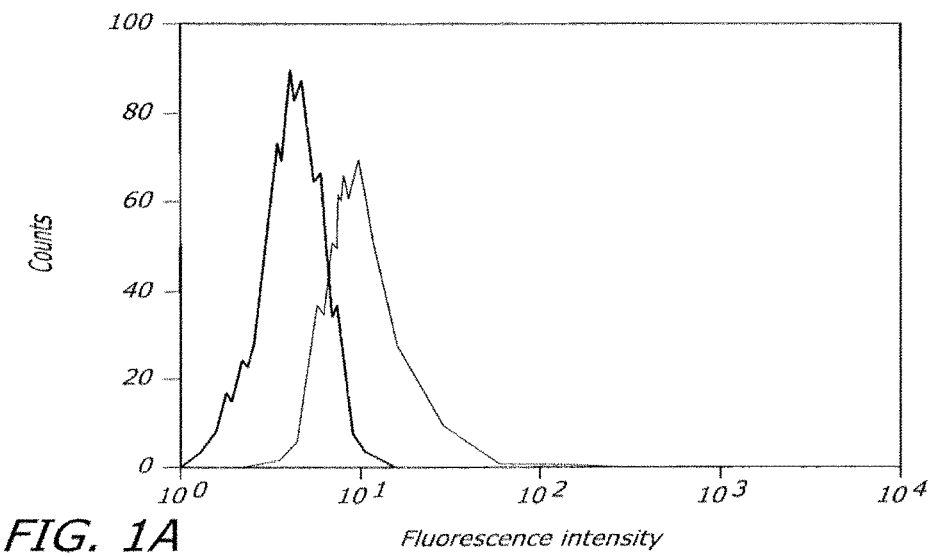
FIG. 1(A) shows flow cytometry analysis of Jurkat cells treated with Fuc alkynyl-derivatized analogs and labeled with biotin/fluorescein conjugated streptavidin (filled trace, untreated cells; black, cells treated with Fuc 3; grey, cells treated with alkynyl-derivatized Fuc 1).
Figure 1B:
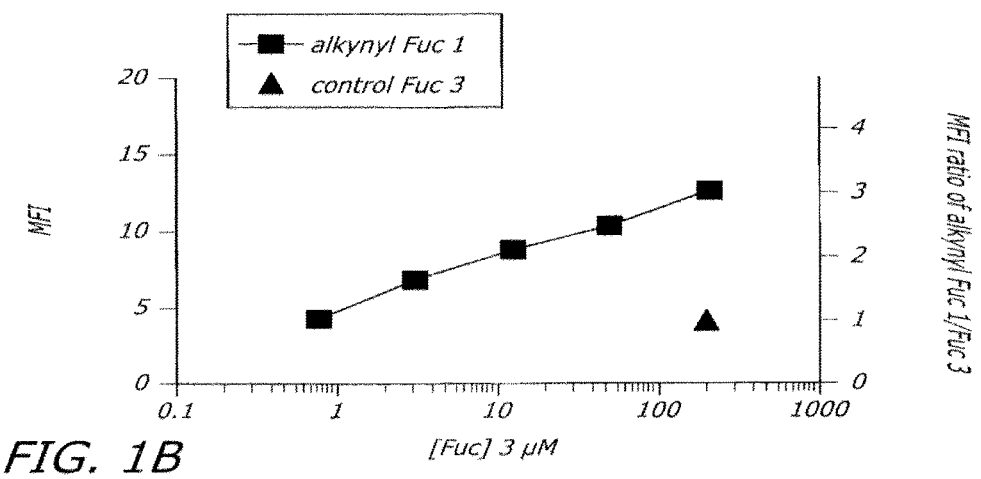
FIG. 1(B) shows dose-dependency of fucosyl-glycan tagging by alkynyl-derivatized Fuc 1 over 3 days.
Figure 1C:
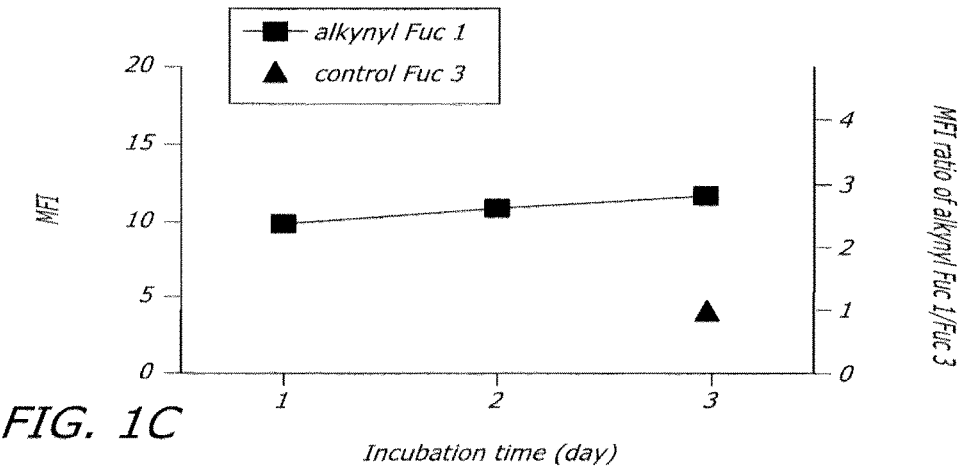
FIG. 1(C) shows the time course of fucosyl glycan tagging by 200 micromolar alkynyl Fuc 1.
Figure 1D:
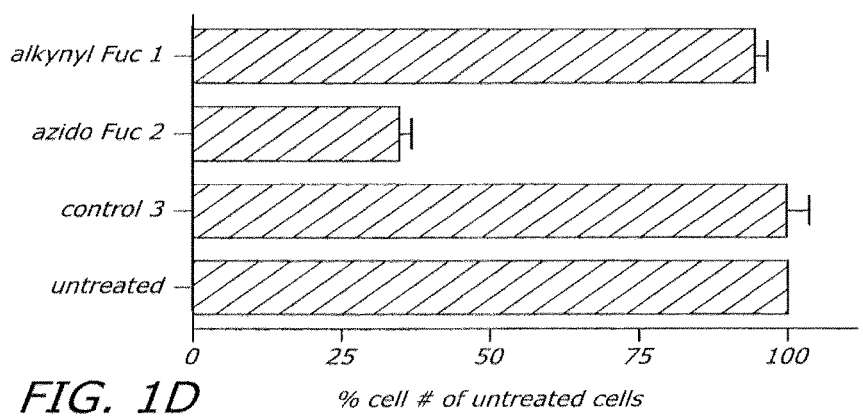
FIG. 1 shows analysis of cells labeled with Fuc analogs.

It is also disclosed how treatment with exogenous Fuc analog affects cell growth rate. As shown in FIG. 1D, the number of cells after 3 days is similar whether they are treated with 200 micromolar alkynyl Fuc 1, 200 micromolar Fuc 3, or grown without exogenous Fuc. In contrast, the addition of 200 micromolar azido Fuc 2 inhibits cell growth considerably, by 65% when compared with the untreated cells. These results indicate that azido Fuc 2 analog, which was used previously for probing fucosylation, is more toxic to cells than alkynyl Fuc 1 analog. Such toxicity may lead to global change in expression, therefore a nontoxic probe is preferable for accurate probing of glycoconjugate expression.

Previously, it was demonstrated that the majority of an exogenous ManNAc analog, N-levulinoylmannosamine, acquired by cells is converted into sialic acid via biosynthetic pathways.

Figure 2A:
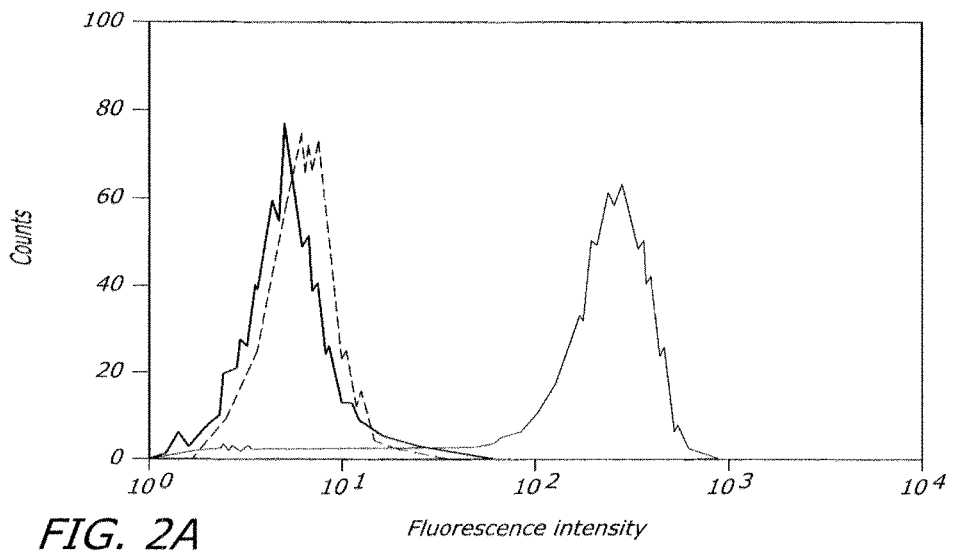
FIG. 2(A) shows flow cytometry analysis of Jurkat cells tagged with derivatized alkynyl-derivatized ManNAc (filled trace, untreated cells; green, cells treated with control 5; purple, cells treated with alkynyl ManNAc 4).
Figure 2B:
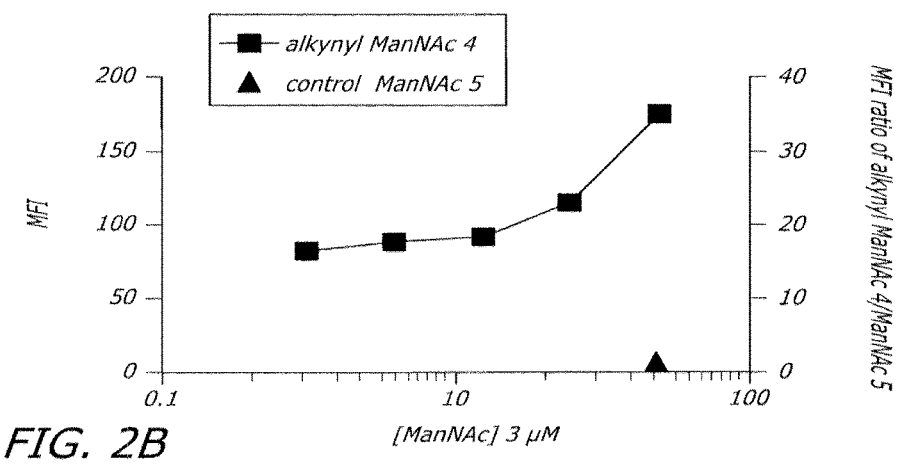
FIG. 2(B) shows dose dependency of sialyl glycoconjugate tagging with alkynyl-derivatized ManNAc 4 for 3 days.
Figure 2C:
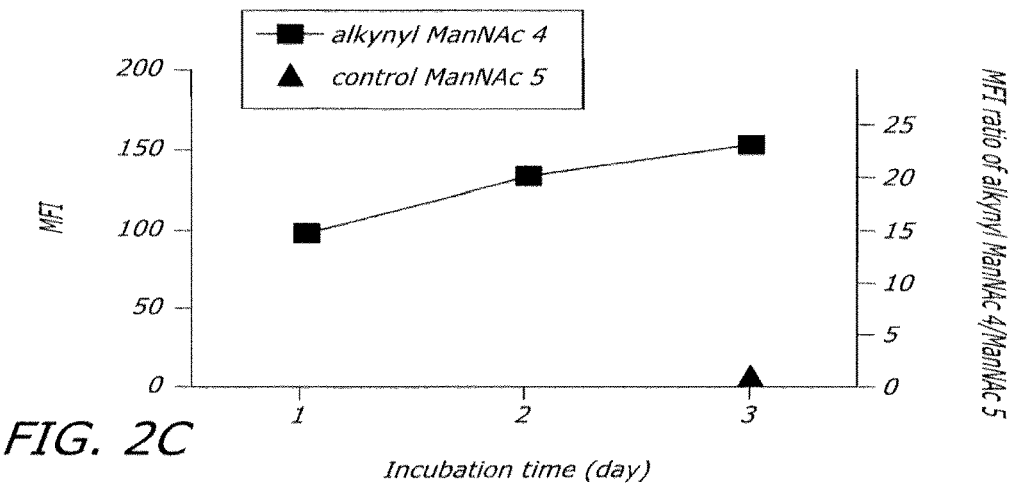
FIG. 2(C) shows time course for tagging sialyl glycoconjugates by treatment with 25 micromolar alkynyl-derivatized ManNAc 4.
Figure 2D:
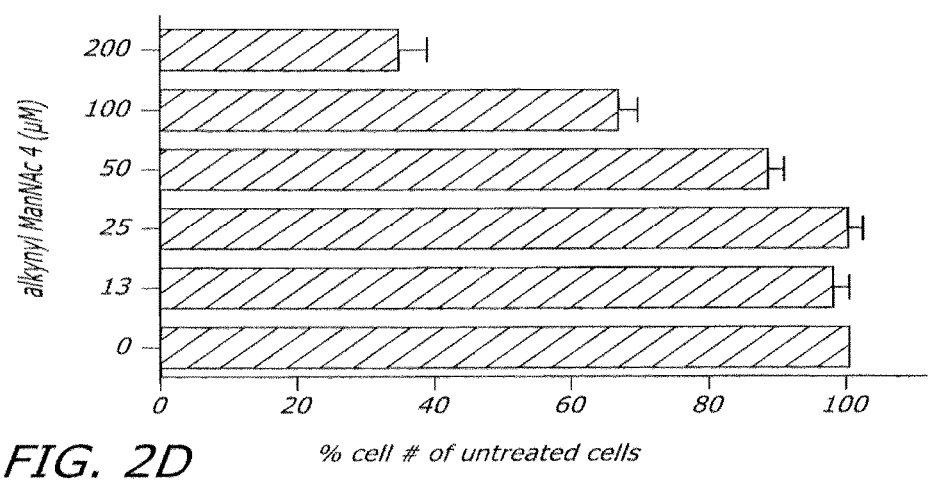
FIG. 2(D) shows growth rate of Jurkat cells treated with different doses of alkynyl-derivatized ManNAc 4 after 3 days.

It is now disclosed in one exemplary implementation of the disclosure that treating cells with derivatized alkynyl ManNAc 4 results in derivatized alkyne-bearing sialyl glycoconjugates. In one aspect of the method, cells are treated with 4 at various concentrations for one to 3 days. Modified sugar analogs and probes used in this disclosure are shown in Scheme 1. Tagging of the cell surface glycoconjugates by derivatized alkynyl ManNAc is illustrated in FIG. 2. FIG. 2 shows analysis of cells labeled with ManNAc analogs analyzed by monitoring fluorescence intensity with flow cytometry after clicking on the biotin azide probe 6 and staining cells with fluorescein-conjugated streptavidin. Labeling with derivatized alkynyl ManNAc 4 yielded a specific signal on the cell surface compared with the control values obtained from cells treated with control ManNAc 5 (FIG. 2A). Dose-dependent labeling was observed in cells treated with derivatized alkynyl ManNAc 4 (FIG. 2B). Compared with the MFI of controls, there was significant labeling on cells treated with derivatized alkynyl ManNAc 4, even at concentrations as low as 3 micromolar (15-fold increase). Time-course experiments revealed that treatment with derivatized alkynyl ManNAc 4 from one to three days gave a 15- to 23-fold increase in labeling intensity over control levels (FIG. 2C). The optimal concentration of 4 for tagging sialyl glycoconjugates falls between 25 and 50 micromolar. In this concentration range, 4 showed little or no toxicity, although it is more toxic above 100 micromolar (FIG. 2D).

One of the advantages of labeling an alkynyl-derivatized sugar tagged glycoconjugate with an azido-derivatized probe via CuAAC, or the click reaction, is the formation of a triazole unit, which can modulate the fluorescent emission of probes through electron-donating properties. It was previously shown that such click-activated fluorescence is useful in fluorescently labeling azido Fuc-bearing glycoconjugates using a 1,8-naphthalimide-alkyne probe. However, the azido version of the naphthalimide probe causes high background, making it less useful for labeling our alkynyl sugars.

Figure 3A:
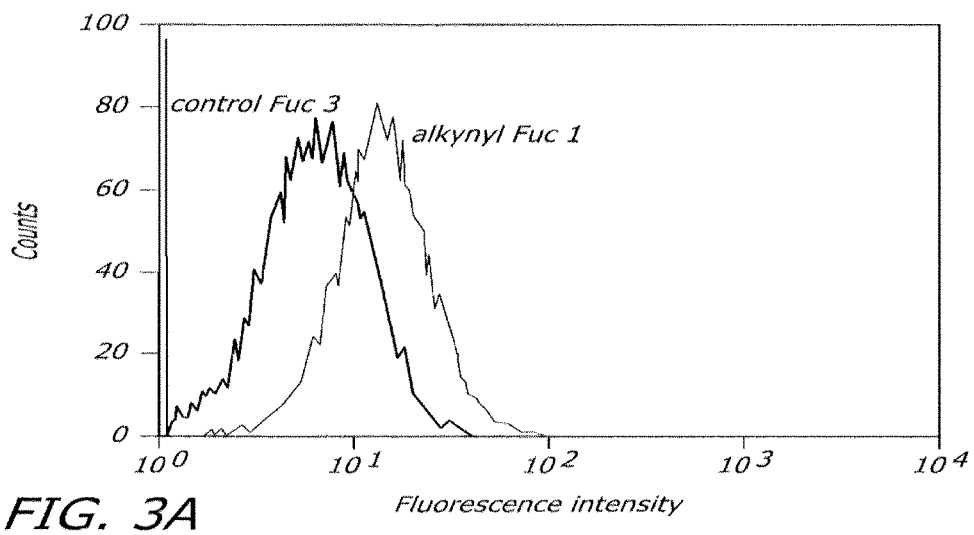
FIG. 3 shows tagging of cell surface glycans by derivatized alkynyl sugar analogs and subsequent labeling with probe 3-azido-7-hydroxycoumarin 7. Shown is flow cytometry analysis of Jurkat cells tagged with 200 micromolar derivatized alkynyl Fuc 1 (A) or 25 micromolar alkynyl-derivatized ManNAc 4 (B) for 3 days. The fluorescence intensity was detected after labeling with a coumarin probe 7. Filled histogram, cells treated with control sugar analog 3 or 5; open histogram, cell treated with alkynyl-derivatized sugar 1 or 4.
Figure 3B:
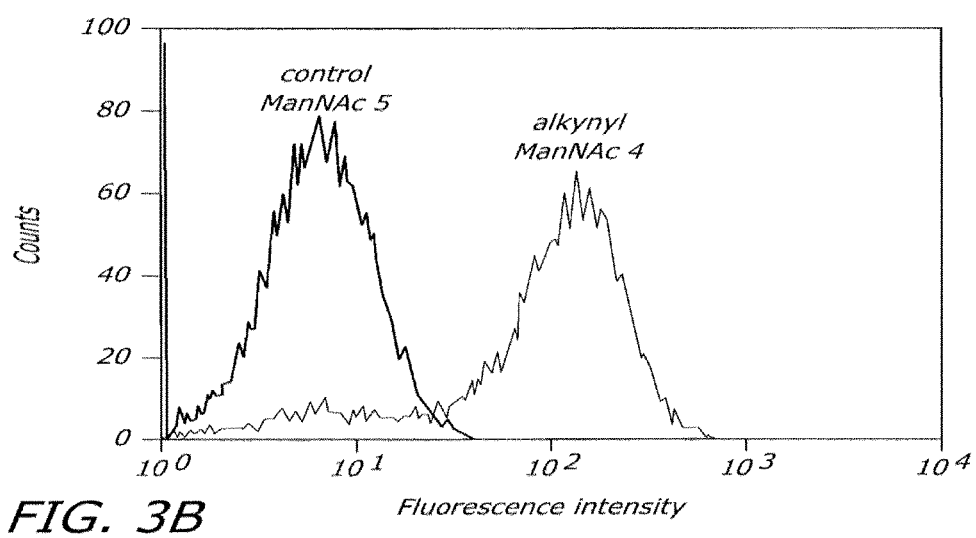

Recently, another click-activated azido-deritatized fluorescent probe, based on coumarin, was reported in the literature. In one aspect of the disclosure, the fluorogenic probe, 3-azido-7-hydroxycoumarin 7, is used as the coupling partner for alkynyl tags on labeled glycoconjugates. As shown in FIG. 3, cells treated with derivatized alkynyl Fuc 1 (FIG. 3A) or derivatized alkynyl ManNAc 4 (FIG. 3B) allowed significant fluorescent labeling after reacting with a 3-azido-7-hydroxycoumarin probe, whereas cells treated with control sugars 3 and 5 gave very low background signals, evidencing low reactivity with a 3-azido-7-hydroxycoumarin probe.

Visualization of Fluorescently Labeled Glycoconjugates in Cells.

Figure 4:
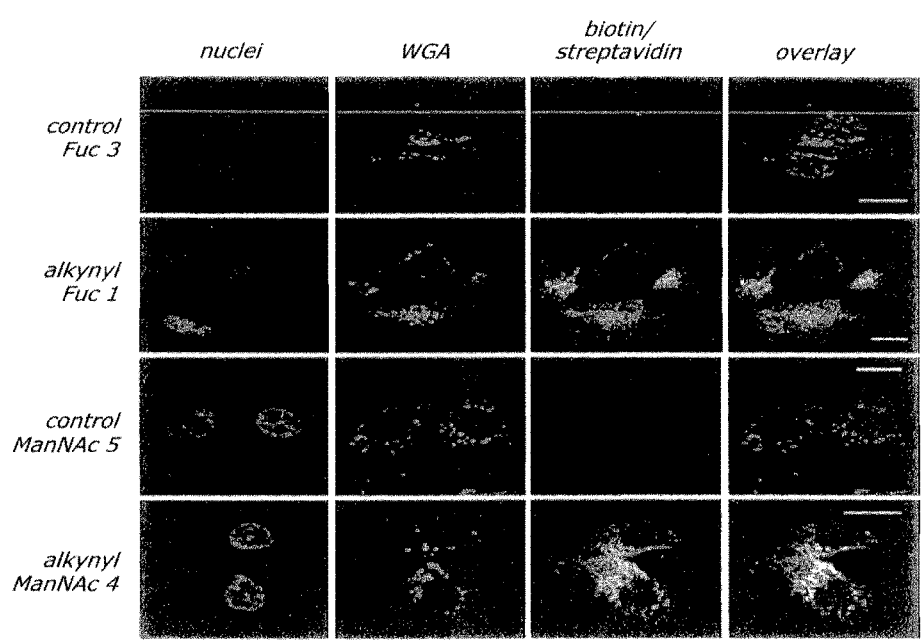
FIG. 4 shows fluorescent imaging of fucosyl and sialyl glycoconjugates in cells. Confocal microscopy of Hep3B cells treated with 200 micromolar Fuc analogs or 25 micromolar ManNAc analogs. Cellular glycoconjugates were biotin-labeled and stained with streptavidin (fluorescein, green), WGA lectin (Alexa Fluor 594, red), and Hoechst 33342 (blue). (Scale bars: 20 micrometer).
Figure 5:
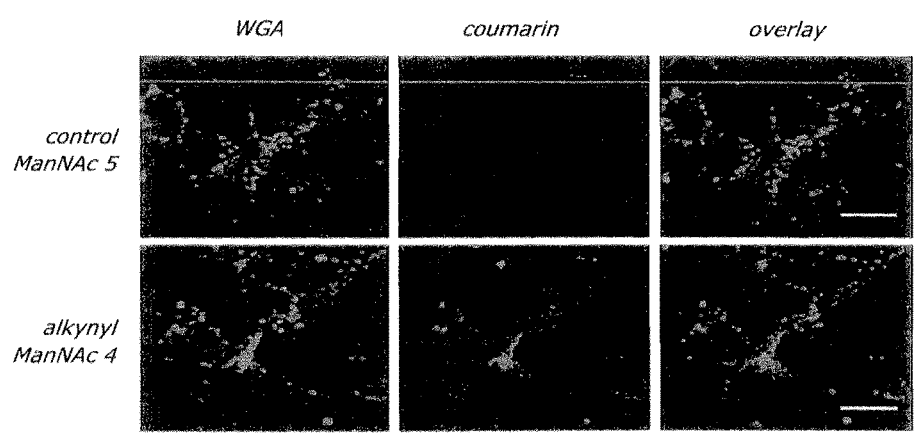
FIG. 5 shows visualization of derivatized alkynyl-tagged sialyl glycoconjugates in cells using "click-activated" fluorogenic labeling. 7. Shown is confocal microscopy of coumarin-labeled Hep3B cells. Cells were treated with 25 micromolar derivatized ManNAc 5 or 4 for 3 days, and then labeled with fluorogenic coumarin probe 7 (blue) and stained with WGA lectin (Alexa Fluor 594, red). (Scale bars: 20 micrometer).

One exemplary implementation of the disclosure provides a method to visualize the localization of glycoconjugates using alkynyl sugar tagging. To visualize the localization of glycoconjugates tagged with alkynyl sugars, adherent cells are grown on slides in the presence or absence of derivatized alkynyl sugars. After a 3-day-incubation, cells attached to the slides are fixed, permeabilized, and labeled with either biotin probe 6 or fluorogenic probe 7 for fluorescent signal analysis with confocal microscopy (FIGS. 4, 5, 10 and 11). For comparison, samples are also stained with wheat germ agglutinin (WGA, a Golgi marker) and Hoechst 33342 (marker for cell nuclei). In one aspect of the method, cancer cell lines, such as Hep3B (hepatocellular carcinoma) and MCF-7 (breast adenocarcinoma) cells, are treated with derivatized alkynyl Fuc 1 to result in a strong punctate-labeling signal after labeling tagged glycoconjugates with a biotin probe 6 and staining with fluorescein-conjugated streptavidin. This signal shows significant overlap with the WGA signal, indicating the labeled fucosyl glycoconjugates are localized in Golgi apparatus (FIGS. 4 and 10). Similar results are obtained from cells treated with alkynyl ManNAc 4, which probes for tagged sialic acid-containing glycoconjugates, when labeled by biotin probe 6 and fluorogenic probe 7 (FIGS. 4, 5, 10 and 11). Consistent with the results from flow cytometry, confocal microscopic analysis of cells treated with control sugars 3 and 5 gives very low background after reacting with click probes, confirming the labeling of alkynyl containing glycoconjugates is specific and sensitive.

Labeling of Glycoconjugates in Cell Extract.

Figure 6A:
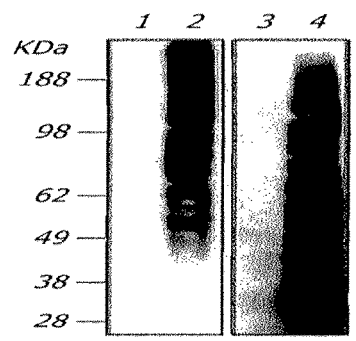
FIG. 6 shows detection of derivatized alkynyl-tagged glycoconjugates in cell extracts subjected to Western blot. Glycoconjugates tagged with derivatized alkynyl sugars were labeled and subsequently detected by immunoblotting of biotin tag (A) or fluorescent imaging of fluorogenic coumarin probe 7 (B). Protein extracts from cells grown with different sugars were analyzed (lane 1, control Fuc 3; lane 2, alkynyl-derivatized Fuc 1; lane 3, control ManNAc 5; lane 4, alkynyl-derivatized ManNAc 4). The protein gel (4-12%) was subsequently stained by Coomassie blue after fluorescent imaging, to verify equal protein loading.
Figure 6B:
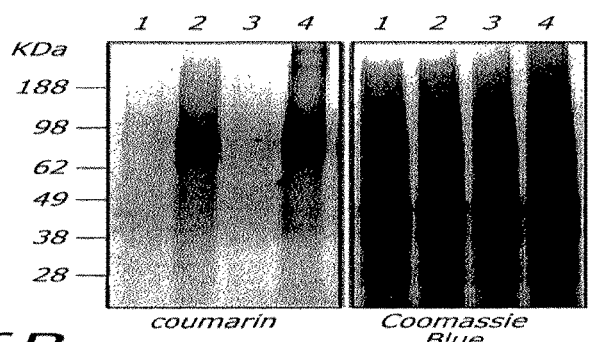

Because the herein disclosed labeling system enables the identification of cellular glycoconjugates, it can also serve well in glyco-proteomic applications aimed at discovering unknown glycosylated targets for diagnostic and therapeutic purposes. In one aspect of the disclosure, cell extracts are analyzed after growing cells in a medium containing alkynyl-derivatized sugars to demonstrate the detection of individual labeled proteins. Soluble lysate fractions are labeled with biotin probe 6, fluorogenic probe 7, or a standard azido-derivatized rhodamine probe used in proteomics before separating proteins by SDS/PAGE. As shown in FIG. 6A, specific biotin-labeling signals were detected by Western blot in proteins from cells treated with alkynyl sugars 1 and 4. Positive fluorescent signal was also detected in alkynyl positive protein lysate when labeled with fluorogenic 3-azido-7-hydroxycoumarin 7 and rhodamine probes (FIG. 6B and FIG. 11). Proteins harvested from cells grown with control sugars 3 and 5 and processed utilizing the same cycloaddition labeling process, showed little to no signal by Western blot or fluorescence. The labeling patterns for Fucyne and ManNAcyne are notably different, indicating the detection of unique glycoconjugates. The data herein presented demonstrate the feasibility and utility of labeling and identifying individual glycoconjugates by using this probing system. Moreover, further processing, including a streptavidin/avidin enrichment or gel slice purification, will allow for comparative identification by proteomic mass spectrometry techniques of unknown glycoconjugates expressed at different cell status, for instance, un-differentiated verses differentiated cells, or normal verses cancer cells.

The ability to visualize and isolate cellular glycoconjugates is useful to deconvolute the complexity and microheterogeneity that make it difficult to study their biological function. Toward this goal, several metabolic oligosaccharide engineering techniques have been developed, wherein the endogenous biosynthetic machinery for glycosylation is exploited to insert sugar analogs in place of their native counterparts. The tagged glycoconjugates, which contain bioorthogonal chemical handles, can then be chemoselectively labeled with a complementary reactive probe for further manipulation, including visualization or isolation. Recently, we designed a system for incorporating derivatized 6-azido derivatized Fuc analogs as cellular glycoconjugate "tags" with subsequent labeling with alkynyl-derivatized probes using CuAAC. We also introduced the use of this process for selective and specific labeling of modified glyconjugates at the cell surface as well as in intracellular environments. Here, we have expanded the scope of our specific glycoconjugate tagging system by establishing that another useful chemical reporter, the alkyne group, can also be used to "tag" cellular glycoconjugates when appended on Fuc and ManNAc derivatives. Similar to its azide counterpart, the alkyne is a small, inert, bioorthogonal group that can be chemoselectively labeled by using click chemistry. The presently disclosed alkynyl Fuc and ManNAc saccharides represent a robust platform for labeling fucosylated and sialylated glycoconjugates in vivo. Formerly, azide sugar analogs were incorporated into glycoconjugates. However, it has been found that the azido Fuc analog is quite toxic to cells at the levels required for efficient labeling, which might in turn lead to aberrant cellular glycan profiles. The alkynyl Fuc, on the other hand, is much less toxic, yielding higher signals and less background, when cellular incorporation was monitored by flow cytometry. Alkynyl-derivatized ManNAc is not toxic at the low levels of the modified sugar required for efficient glycoconjugate labeling as observed by flow cytometry and microscopy. Without being bound by theory, this likely reflects the higher relative abundance of sialic acid verses Fuc residues. The alkynyl sugars also are efficient ligation partners for click activated fluorogenic and standard click probes. Tagging with click-activated probes is particularly useful because of the generation of an instant signal upon ligation with modified glycoconjugates that does not produce any significant background. As established by each of the herein described visualization methods (flow cytometry, confocal microscopy, and SDS/PAGE), the signal generated by the click-activated probe is equivalent to that of the biotin-secondary detection systems; however, it requires one less incubation step and no washing. Furthermore, the click-activated probes are small and hydrophobic, making them more amenable to intracellular penetration and tagging in living cells. The utility of this approach for probing interesting glycoconjugates was demonstrated by treating several human cancer cell lines with the alkynyl sugar substrates and subjecting them to several methods of analysis. In all cases, fluorescent-labeling of cell surface glycoconjugates is witnessed by flow cytometry. Information about intracellular glycoconjugate labeling and localization was determined by using confocal microscopy. Here, it is demonstrated that both alkynyl Fuc and ManNAc modified glycoconjugates are localized in the Golgi, consistent with their proposed site of transfer. Notably, detailed analysis of microscopy images can supply quantitative data within regions of colocalization, which may provide a useful tool for monitoring glycoconjugate levels and trafficking.

In another aspect, individual modified glycoconjugates can be separated and visualized by SDS/PAGE analysis, setting the stage for further proteomic analysis. In future studies, we plan to extend and combine these methodologies to obtain information about cellular glycoconjugates under different physiological disease states and cellular statuses, such as stress, apoptosis, or inflammation. Comparative studies between various stages of cancer progression, in addition to pulse-chased techniques to follow the dynamics of newly synthesized proteins within individual cellular systems should provide much needed snapshots of critical glycoconjugate behavior. Indeed, in preliminary studies with prostate cancer cells, we observed an increase in the fucosylated glycoconjugate signal when compared with noncancerous prostate controls (FIG. 10). This indicates that there might be some interesting correlations between increased Fuc expression and prostate cancer, a fact that is already well known for numerous cancers. Notably, it is important to consider that the introduction of modified sugars might change the cellular activity of certain glycoconjugates. Perturbations in glycoconjugate-mediated binding have been noted with viral receptors and lectin interactions in metabolic oligosaccharide engineering studies where sialic acid derivatives were introduced into cellular glycoconjugates. Accordingly, these studies also found that some Fuc lectins, including aleuria aurantia lectin (AAL; specific for alpha-1,6- or alpha-1,3-linked Fuc) and Ulex Europaeus Agglutinin I (UEA-1; specific for alpha-1,2-linked Fuc), bound with significantly lower avidity among cells treated with alkyne Fuc verses control (FIG. 11). These results are not surprising, considering that a change from a methyl to a more bulky alkynyl group may interfere with the recognition in the small conserved hydrophobic pocket found in many Fuc lectins. Indeed, in some cases, altered biological responses may prove useful for perturbing and profiling the function of unknown carbohydrate binding proteins. On the other hand, some glycoconjugate modifications do not seem to greatly affect binding interactions, past studies analyzing the binding of selectins to synthetic analogues of sialyl Lewis x showed a significant tolerance for N-acyl modification on sialic acid. Thus, the analysis of cells treated with modified sugars over an extended period must be evaluated carefully. To circumvent any artifacts from altered activity or differential cellular uptake, pulse-chase experiments may be useful. These experiments would result in lower levels of modified glycoconjugates, while presenting a comparable cell-to-cell snap shot of glycoconjugate behavior.

The usage of alkynyl sugars is further applied to analyze tagged glycoproteomes through metabolic oligosaccharide engineering (MOE) in *Helicobacter pylori* (*H. pylori*). Although rare among prokaryotes, Gram-negative bacterium *H. pylori* possesses the glycosylation machinery necessary to fucosylate its glycoconjugates. This fucosylation process can produce Lewis antigens, among other structures, on glycoconjugates and enables *H. pylori* to bind to host cells and subsequently evade the host immune system, thus contributing to persistent infection in stomach. MOE strategy provides the opportunity to study fucosylated glycoconjugates of clinical *H. pylori* isolates from various stages of infection, so that the link between fucosylation and the development of gastric ulcer and cancer.

Figures 13A, 13B:
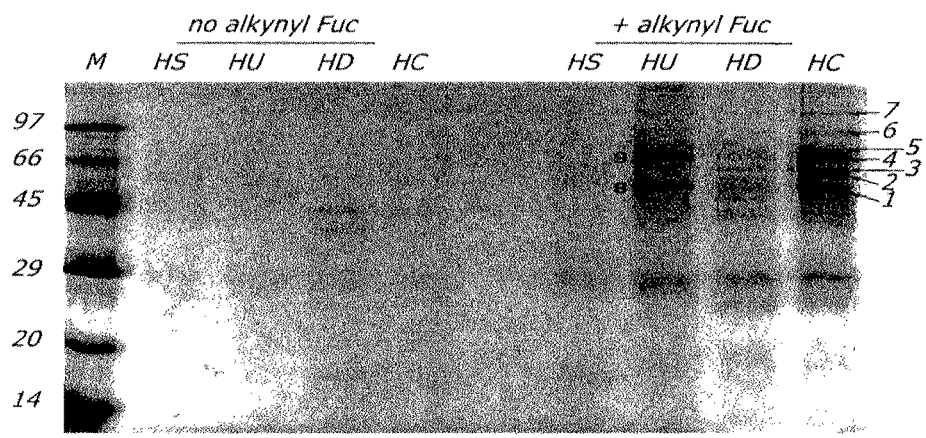

Representative *H. pylori* strains isolated from human gastric biopsy specimens, including gastritis (HS), duodenal ulcer (HD), gastric ulcer (HU) and gastric cancer (HC), were subjected to MOE: all the strains were grown on CDC agar plate supplemented with 200 micromolar derivatized alkynyl Fuc 1 for two days under micro-aerobic atmosphere (5% $O_2$, 15% $CO_2$, 80% $N_2$). Tagged protein extracts were prepared in lysis buffer (1% NP-40, 150 mM NaCl, 100 mM sodium phosphate pH7.5, 1×EDTA-free protease inhibitor cocktail) and subjected to subsequent labeling with biotin probe 6 (protein 1 mg/ml with 0.1 mM azido biotin 6/0.1 mM Tris-triazoleamine catalyst/1 mM $CuSO_4$/2 mM sodium ascorbate in lysis buffer) at room temperature for 1 h. To isolate glycoproteins, 1 mg labeled protein samples were precipitated with 10% TCA for 30 mM to remove excessive biotin probe, re-dissolved in 1 ml of 0.2% SDS/PBS, and immunoprecipitated with 50 µl anti-biotin agarose beads (Vector Laboratories) at room temperature for 1 h Immunoprecipitates were then analyzed by SDS-PAGE and stained for visualization. As shown in FIG. 13A, several proteins were detected in MOE-tagged *H. pylori*, while no proteins were isolated from non-tagged *H. pylori* proteome samples, indicating that the immunoprecipitation process was specific. Notably, more fucosyl proteins were detected in HC and HU strains, and fewer proteins were observed in HS and HD strains. Protein bands revealed in SDS-protein gel (marked with numbers in FIG. 13A) were excised, extracted, reduced, alkylated, tryptic digested to elute peptides and subjected to LC-MS$^2$ analysis for protein identification (FIG. 13B).

To validate the fucosylation of proteins in *H. pylori*, we examined CagA (cytotoxicity-associated immunodominant antigen), a virulence factor reported to associate with malignancy, for the incorporation of alkynyl Fuc 1 by anti-CagA antibody in HC strain as follows: Labeled proteins extracted from control or alkynyl Fuc 1-treated HC samples were subsequently labeled via-cycloaddition with biotin probe, followed by immunoprecipitation with anti-CagA antibody. The biotinylated Fuc tags present on CagA protein were revealed by peroxidase-conjugated streptavidin on protein blot. By comparison with the CagA protein isolated from a control sample (derived from cells grown without alkynyl Fuc 1), a specific signal is only detected in MOE-tagged HC strain, indicating the existence of alkynyl Fuc tags on CagA protein (FIG. 14).

Secretory glycoconjugates are known to be continuously recycled. Glycoconjugates are synthesized in the ER/Golgi, and then exported to subcellular locations, primarily the cell-surface, before being endocytosed to the lysome, where they are processed and ultimately taken back to the Golgi to start the cycle again. At this point, the kinetics of these processes are not well understood, and conflicting reports exist. Pulse-chased experiments can be used examine trafficking of glycans, and to monitor the differential trafficking of glycans in cells at different stages of disease. It is worth noting, that by pulsing the sugars cellular perturbations caused by the modified architecture of the akynylated glycans and/or toxicity of the azido-fucose derivative may be reduced by use of lower concentrations and time exposure to derivatized sugars.

Pulse-chased MOE experiments entail growing cells of interest to log-phase levels and then exposing them to the sugar analogs in the growth medium, as prescribed by standard MOE, but only for a 30 minute pulse, before replenishing with fresh medium devoid of sugars. Post sugar-pulse, the cells are grown for various lengths of time before analysis. FIG. 15 shows microscopy of Hep3B cells subjected to pulse-chase conditions with Fucyne, CuAAC labeled with biotin, and detected by streptavidin-FITC. The signal for the fucosylated glycans (green) may emerge as a co-localized yellow signal as early as 2 h, indicating significant overlap with the Golgi marker (red). A pure green signal may increase over longer periods following the Fucyne pulse, indicating a progression from the golgi to the cell surface (data that may be obtained for sialylated alkynyl glycans shows a similar trend). Notably, this progression from Golgi to cell surface using copper free click-reactions, label cell-surface glycans.

For example, by coupling the pulse-chase procedure with cellular markers of interest (e.g., to image the lysome with LysoTrackerRed, the Golgi with BODIPY ceramide TR, the endsome with Alexafluor-labeled transferrin, or the ER with R6-rhodamine B hexyl-ester chloride) information may be obtained about dynamics and trafficking of glycans in cancer cells. Using orthogonal sugar probes, for instance FucAz and ManNAcyne (or Fucyne and azido sialic acid derivatives), in combination with probe fluorophores that emit at different wavelengths, may allow for simultaneous labeling and imaging of both sugars in the same sample. A combination of copper-free and CuAAC may also provide more in-depth information about cellular trafficking. Pulsing Fucyne and then azido-derivatized sugars may provide more information about spatial and temporal trafficking of fucosylated glycoconjugates (First pulse at the cell surface, while second pulse is in ER, etc). Finally, Double labeling with FucAz and ManNAcyne may be used to monitor the trafficking of fucosylated verses sialylated glycans, this data may be further used to quantify, contrast and compare the relative numbers of fucosylated verses sialylated verses fucosylated and sialylated glycans found at a cell in various life cycle stages.

In one exemplary implementation of the disclosure, an Intermediary of Azido Derivatized Fucose is 6,7-Deoxy-1,2:3,4-di-O-isopropylidene-α-L-galacto-hept-6-ynopyranoside A suspension of PCC (1.3 g, 6.0 mmol), NaOAc (1.0 g, 12.0 mmol) and 4 .ANG. molecular sieves (2.7 g) in dry $CH_2Cl_2$ (18 mL) was stirred for 1 h. To this mixture was added a solution of 17 (520 mg, 2.0 mmol) in dry $CH_2Cl_2$ (9 mL) dropwise, and the mixture was stirred at room temperature for 2 h. The reaction mixture was diluted with hexane/ether (1:1, 50 mL), and the solution was filtered through a bed of silica gel. The filtrate was concentrated to give the crude aldehyde. To a suspension of tBuOK (471 mg, 4.2 mmol) in dry THF (5 mL) was added a solution of $(EtO)_2P(O)CHN_2$ (748 mg, 4.2 mmol) in THF (5 mL) at −78° C. and the mixture was stirred at 5 min under $N_2$ gas. To this solution, a solution of the aldehyde in THF (5 mL) was added, and the mixture was allowed to warm to room temperature and continued to stir overnight. The reaction mixture was quenched with 100 mL of water, and the mixture was extracted with $CH_2Cl_2$. The extracts were washed with brine, dried over with $Na_2SO_4$, and evaporated. The residue was purified by flash column chromatography on silica gel (AcOEt/hexane 1:5) to afford 4 as a colorless oil (295 mg, 62%).

In conclusion, herein disclosed is a mehod for metabolic oligosaccharide engineering that can incorporate alkyne-bearing sugar analogs in cellular glycoconjugates. The utility of the alkynyl system has been demonstrated by incorporating Fuc and ManNAc derivative sugars into cancer cell lines, where they were visualized at the cell surface, intracellularly, and as individual glycoconjugates. The alkynyl Fuc sugar was also incorporated into fucoysylated cellular glycans produced by *H. pylori*, a causative agent of gastric cancer. Sugars were selected that report on Fuc (alkynyl Fuc) and sialic acid (alkynyl ManNAc) because these residues, in particular, have been linked to many aberrant glycoconjugates in cancer. Although several glycan epitopes binding sialic acid and fucose are known, there are likely many other as yet unidentified glycoconjugates and glycan activities that contribute. Identification of these glycan-related biomarkers and targets for therapeutic intervention is one of the key objectives in our strategy.

EXAMPLES

All chemicals were purchased as reagent grade and used without further purification. Reactions were monitored with analytical thin-layer chromatography (TLC) on silica gel 60 F254 plates and visualized under UV (254 nm) and/or by staining with 5% sulfuric acid or acidic ceric ammonium molybdate. $^1$H- or $^{13}$C-NMR spectra were measured on a Bruker DRX-500 or DRX-600 using $CDCl_3$ or DMSO-$d_6$ as the solvent (1H, 500 or 600 MHz; $^{13}$C, 125 or 150 MHz). Chemical shifts (in ppm) were determined relative to either tetramethylsilane (0 ppm) or deuterated chloroform (77 ppm). Mass spectra were obtained by the analytical services of The Scripps Research Institute. Biotin-conjugated Aleuria Aurantia Lectin (AAL), fluorescein-conjugated streptavidin, and fluorescein conjugated Ulex Europaeus Agglutinin I (UEA-1) was purchased from Vector laboratories (Burlingame, Calif.). RPMI 1640, DMEM, Alexa Fluor® 594-conjugated WGA lectin, and Hoechst 33342 were purchased from Invitrogen (Carlsbad, Calif.). SuperBlock® Blocking buffer, peroxidase-conjugated goat anti-mouse IgG, and SuperSignal® Chemiluminescent Substrate were obtained from Pierce (Rockford, Ill.). EDTA-free protease inhibitor cocktail and anti-biotin MAb were purchased from Roche Applied Science (Indianapolis, Ind.).

FCS is Fetal Calf Serum. DMEM is Dulbecco's Modified Eagle Medium. RPMI 1640 is Roswell Park Memorial Institute Medium 1640. CDC Agar plate is the CDC formulation of Remel Anaerobic Blood Agar plate, the formulation developed by CDC scientists (Dowell, V. R, and Hawkins, T. M, *Laboratory Methods in Anaerobic Bacteriology*, CDC Laboratory Manual, U.S. Dept. of H.H.S. and CDC, Atlanta, Ga., 1974).

Example 1

Synthesis of 1,2,3,4-tetraacetyl alkynyl fucose (Fuc) (1, mixture of anomers; Scheme 2)

Figure 7:
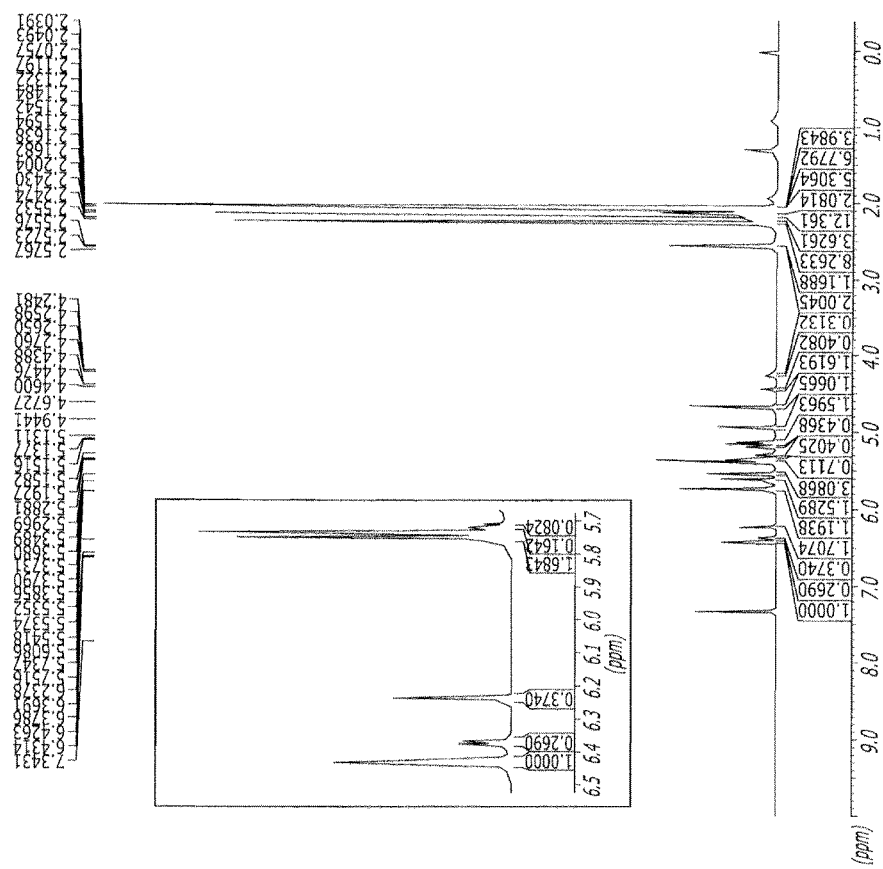
FIG. 7 shows $^1$H-NMR spectra of peracetylated alkynyl Fuc 1.
Figure 8:
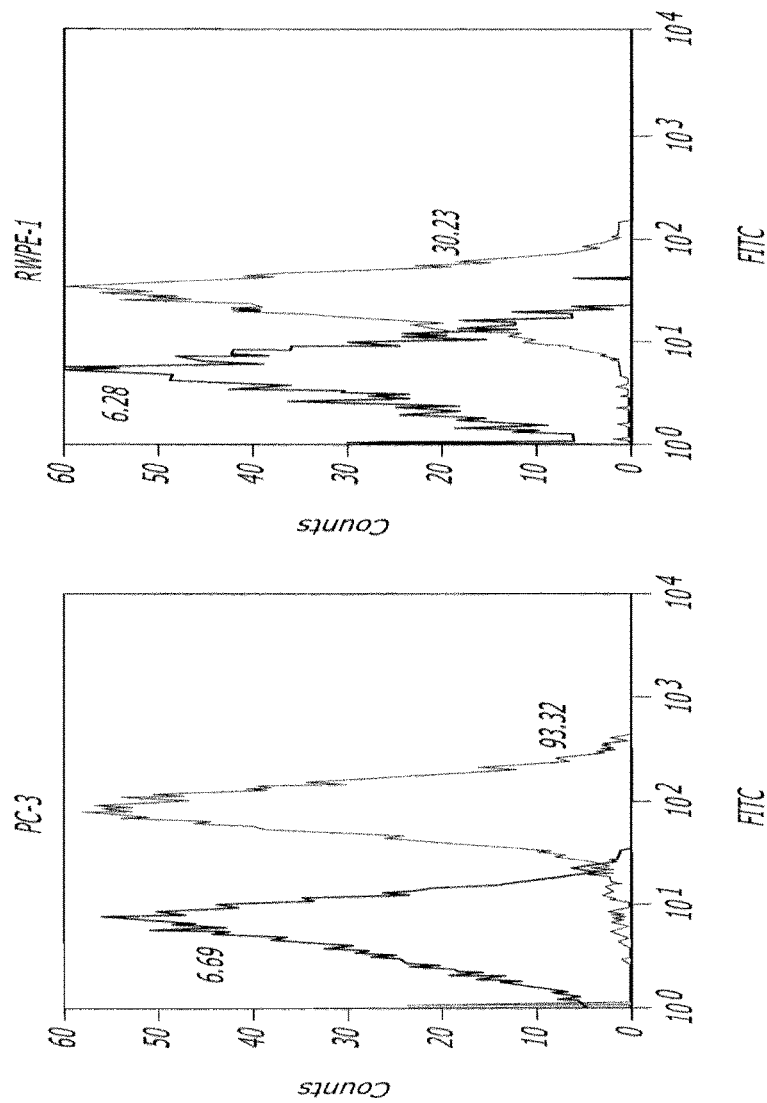
FIG. 8 shows tagging of fucosyl glycans with derivatized alkynyl sugars on prostate cancer PC-3 and RWPE-1 prostate cells. Cells were treated with alkynyl-derivatized Fuc analog 1 or 3, labeled with azido-biotin probe 6, and subjected to flow cytometry analysis. Filled histograms.

To a flask containing compound 8 (0.05 g, 0.2 mmol), TFA solution (1 ml, 90% TFA in $H_2O$) was slowly added at 0° C. The reaction was stirred on ice for 1 h and concentrated in vacuo. The resulting residue was treated with pyridine (1 ml), N,Ndimethylaminopyridine (2.0 mg), and acetic anhydride (1 ml), stirred overnight, concentrated, and diluted with dichloromethane. This solution was then sequentially washed with 1 N aqueous HCl, saturated aqueous $NaHCO_3$, and brine. The organic phase was dried over anhydrous $Na_2CO_3$ and concentrated. Silica gel chromatography gave product 1 (0.055 g, 80%, α-pyranoside:β-pyranoside: α-furanoside:β-furanoside=30:51:11:8) as a colorless gum (FIG. 7). Partial $^1$H-NMR of mixture (500 MHz, $CDCl_3$) δ 5.74 (d, J=8.4 Hz, H-1 (β-pyr)), 6.24 (s, H-1 (α-fur)), 6.36 (d, J=4.8 Hz, H-1 (β-fur)), 6.43 (d, J=2.6 Hz, H-1 (α-pyr)); ESI-TOF-HRMS m/e calculated for $(M+Na)^+$ $C_{15}H_{18}O_9Na$ 365.0843; found 365.0839.

Example 2

Synthesis of N-4-pentynoylmannosamine (10, Mixture of Anomers; Scheme 3)

A mixture of D-mannosamine hydrochloride (863 mg, 4.0 mmol), N-succinimidyl 4-pentynoate 9 (781 mg, 4.0 mmol), triethylamine (1.67 ml, 12.0 mmol) in DMF (31 ml) was stirred at room temperature overnight. The reaction mixture was concentrated in vacuo, and the residue was purified by flash column chromatography ($CHCl_3$/MeOH 8:1) to give N-4-Pentynoylmannosamine, 10 (898 mg, 87%); $^1$H-NMR (500 MHz, $D_2O$) 2.37 (t, 2.63H, J=2.5 Hz), 2.48-2.63 (m, J=10.5H), 3.38-3.42 (m, 1H), 3.52 (t, 1H, J=10 Hz), 3.63 (t, 1.63H, J=10 Hz), 3.69-3.91 (m, 7.89H), 4.05 (dd, 1.63H, J=4.5 and 10 Hz), 4.35 (dd, 1.63H, J=1.5 and 4.5 Hz), 4.47 (dd, 1H, J=1.5 and 4.5 Hz), 5.03 (d, 1H, J=1.5 Hz), 5.13 (d, 1.63H, J=1.5 Hz); $^{13}$C-NMR (125 MHz, $D_2O$) δ 14.78, 14.91, 34.62, 34.79, 53.67, 54.50, 60.91, 60.93, 67.01, 67.28, 69.25, 70.56, 70.71, 72.47, 72.50, 76.80, 84.04, 84.45, 93.36, 93.67, 175.68, 176.41; ESI-TOF-HRMS m/e calculated for $(M+H)^+$ $C_{11}H_{17}NO_6$ 260.1129; found 260.1120.

Example 3

Synthesis of 1,3,4,6-tetra-O-acetyl-N-4-pentynoylmannosamine (4, Mixture of Anomers; Scheme 3)

A mixture of 10 (123 mg, 0.500 mmol) and acetic anhydride (0.227 ml, 2.40 mmol) in pyridine (4 ml) was stirred at room temperature overnight. The reaction mixture was concentrated in vacuo, and the residue was dissolved in $CH_2Cl_2$ and washed with water. The organic layer was dried over $Na_2SO_4$ and evaporated. The residue was purified by flash column chromatography (AcOEt/Hexane 1:4) to give 1,3,4,6-tetra-O-acetyl-N-4-pentynoylmannosamine, 4 (183 mg, 86%); $^1$H-NMR (500 MHz, $CDCl_3$) δ 2.00 (s, 9H), 2.06 (s, 9H), 2.097 (s, 3H), 2.10 (s, 3H), 2.11 (s, 3H), 2.14-2.18 (m, 3H), 2.19 (s, 6H), 2.46-2.58 (m, 12H), 3.81-3.87 (m, 1H), 4.00-4.15 (m, 5H), 4.23-4.30 (m, 3H), 4.69 (dd, 2H, J=4.5 and 10 Hz), 4.82 (dd, 1H, J=4.5 and 10 Hz), 5.09 (dd, 1H, J=4.5 and 10 Hz), 5.17 (t, 1H, J=10 Hz), 5.23 (t, 2H, J=10 Hz), 5.33 (dd, 2H, J=4.5 and 10 Hz), 5.90 (s, 1H), 6.03 (s, 2H), 6.36 (d, 1H, J=9.5 Hz), 6.54 (d, 2H, J=9.5 Hz); $^{13}$C-NMR (125 MHz, $CDCl_3$) δ 15.29, 15.40, 20.99, 21.01, 21.06, 21.09, 21.15, 21.21, 35.51, 35.72, 49.56, 49.80, 62.55, 62.70, 65.87, 66.07, 69.25, 70.39, 70.54, 70.63, 71.63, 73.69, 83.07, 83.11, 90.98, 92.08, 168.59, 168.81, 170.07, 170.44, 170.51, 170.98, 171.82, 172.15; ESI-TOF-HRMS m/e calculated for $(M+H)^+$ $C_{19}H_{25}NO_{10}$ 428.1551; found 428.1549.

Example 4

Synthesis of 3-azidopropyl biotin amide (6; Scheme 4)

A mixture of D-(+)-biotin (100 mg, 0.41 mmol), 1-azido-3-aminopropane (82 mg, 0.82 mmol) O-(benzotriazol-1-yl)-N,N,N',N'-tetramethyluronium hexafluorophosphate (311 mg, 0.82 mmol) and N,N-diisopropylethylamine (106 mg, 0.82 mmol) in DMF (5 ml) was stirred at room temperature for 2 h. The reaction mixture was concentrated in vacuo, and the residue was purified by flash column chromatography ($CHCl_3$/MeOH 10:1) to give the amide 6 (53 mg, 40%); $^1$H-NMR (400 MHz, DMSO-d$^6$) δ 1.21-1.35 (m, 4H), 1.45-1.55 (m, 3H), 1.60-1.67 (m, 3H), 2.05 (t, 2H, J=7.6 Hz), 2.57 (d, 1H, J=12.6 Hz), 2.82 (dd, 1H, J=4.8 and 12.6 Hz), 3.07-3.10 (m, 3H), 4.10-4.14 (m, 1H), 4.28-4.32 (m, 1H), 6.36 (s, 1H), 6.42 (s, 1H), 7.84 (m, 1H); ESI-TOF-HRMS m/e calculated for $(M+H)^+$ $C_{13}H_{23}N_6O_2S$ 327.1598; found 327.1598.

Example 5

Flow Cytometric Analysis of Fluorescent Labeling on PC-3 Cell Surface

PC-3 cells were grown in RPMI 1640 (Invitrogen) supplemented with 10% FCS and peracetylated alkynyl Fuc 1 or control Fuc 3 for 3 days at 37° C. Cells were then harvested, washed with 1% FCS/PBS, resuspended (5×105 cells) in 100 µl of staining solution (1 µg/ml lectin conjugates in 1% FCS/PBS). Cells were then incubated on ice for 30 min and washed twice with 1% FCS/PBS. Cells stained with biotin-conjugated AAL were subsequently stained with fluorescein-conjugated streptavidin (0.5 µg/sample in 50 µl of 1% FCS/PBS) for 30 min on ice, and washed three times with 1% FCS/PBS. Data were acquired by FACSCalibur, and were analyzed by CellQuestPro software (BD Biosciences).

Example 6

Flow Cytometric Analysis of Fluorescent Labeling on Jurkat Cell Surface

Jurkat cells were cultivated ($2 \times 10^6/10$ ml) in RPMI medium 1640 supplemented with 10% FCS and various concentrations of peracetylated alkynyl sugars 1, 2, or 4 or native sugars 3 or 5, for 1-3 days at 37° C. Cells were then harvested, washed with 0.1% FCS/PBS, and resuspended ($10^6$ cells) in 100 microliters of click reaction solution (0.1 mM biotin probe 6 or fluorogenic probe 7/0.1 mM Tris-triazoleamine catalyst/0.1 mM $CuSO_4$/0.5 mM sodium ascorbate, in PBS). The reaction was incubated at room temperature for 30 min, and then the cells were washed twice with 0.1% FCS/PBS. Cells treated with biotin probe 6 were subsequently stained with fluorescein-conjugated streptavidin (0.5 microgram per sample in 50 microliters of 1% FCS/PBS) for 30 min at 4° C., and washed three times with 1% FCS/PBS. Data were acquired by BD LSR II with FACSDiva software, and were analyzed by CellQuestPro software (BD Biosciences). Detection of fluorescent adduct with probe 7 was monitored with a 408 nm laser and a 440/40 bandpass filter for excitation and emission, respectively.

Example 7

Microscopic Analysis of Fluorescent Labeling in Cells

Human hepatocellular carcinoma cells (Hep3B) or breast adenocarcinoma cells (MCF-7) were seeded onto six-well plates ($3 \times 10^5/2$ ml per well) containing glass coverslips, and were cultivated in 10% FCS/DMEM or 10% FCS/RPMI medium 1640. Growth medium was supplemented with a control sugar (200 micromolar Fuc 3 or 25 micromolar ManNAc 5 and an alkynyl-modified sugar (alkynyl Fuc 1 or alkynyl ManNAc 4 at the same concentration as control sugars). After growing for 3 days, cells on coverslips were fixed and permeabilized with acetone for 10 min, then subjected to the probe labeling reaction: 0.1 mM biotin probe 6 or fluorogenic probe 7/0.1 mM Tris-triazoleamine catalyst/1 mM $CuSO_4$/2 mM sodium ascorbate, in PBS, at room temperature for 30 min. Subsequently, the fixed and labeled cells were rinsed with PBS and stained with Alexa Fluor 594-conjugated WGA lectin (2 micrograms/ml in 5% BSA/PBS) and/or fluorescein-conjugated streptavidin (2 micrograms/ml in 5% BSA/PBS) at room temperature for 30 min. Hoechst 33342 (10 microgram/ml in PBS) was used to stain nuclei. Fluorescent images were captured by Bio-Rad (Carl Zeiss) Radiance 2100 Rainbow laser scanning confocal microscopy system.

Example 8

Labeling and Detection of Glycoconjugates in Cell Extracts

Cells were seeded at $3 \times 10^6/8$ ml per 10-cm dish and treated with control and test sugars (200 micromolar Fuc 3 vs. alkynyl derivatized Fuc 1, or 25 micromolar ManNAc 5 vs. alkynyl derivatized ManNAc 2) in growth medium at 37° C. After 3 days, cell extracts were prepared by resuspending the cells in 1 ml of lysis buffer (1% Nonidet P-40/150 mM NaCl/protease inhibitor/100 mM sodium phosphate, pH 7.5). Protein extract (1 mg/ml) was labeled for 1 h at room temperature (conditions as outlined in microscopic analysis; the azido rhodamine probe was a gift from Benjamin F Cravatt, The Scripps Research Institute). Labeled protein lysate was resolved by SDS/PAGE. For immunoblotting of biotin-labeled glycoconjugates, electrophoresed proteins were transferred onto PVDF membranes, blocked for 20 min with SuperBlock Blocking Buffer, probed for 1 h with anti-biotin MAb (1 microgram/ml), and incubated with peroxidase-conjugated goat anti-mouse IgG (1:7, 500 dilution) for 30 min. Each step was followed by a wash with 0.02% Tween 20/PBS (PBST). Signal was developed with SuperSignal Chemiluminescent Substrate and detected by exposure to x-ray film. For detecting the coumarin-labeled glycoconjugates, gels were examined under 365 nm UV light with a 535+/−50 nm filter. Images were taken by using a BioDoc-It imaging system (UVP). Rhodamine gels were analyzed.

Example 9

Labeling and Detection of Fucosylated Glycoconjugates in H. pylori

H. pylori isolated from clinical gastric specimens: gastritis (HS), duodenal ulcer (HD), gastric ulcer (HU) and gastric cancer (HC) were grown on CDC agar plate supplemented with 200 μM derivatized alkynyl Fuc 1 for two days under micro-aerobic atmosphere (5% $O_2$, 15% $CO_2$, 80% $N_2$).

Protein extracts were prepared in lysis buffer (1% NP-40, 150 mM NaCl, 100 mM sodium phosphate pH 7.5, 1×EDTA-free protease inhibitor cocktail) and labeled with biotin probe 6 (protein 1 mg/ml with 0.1 mM azido biotin 6/0.1 mM Tris-triazoleamine catalyst/1 mM CuSO4/2 mM sodium ascorbate in lysis buffer) via cycloaddition at room temperature for 1 h. Labeled protein samples (1 mg) were then precipitated with 10% TCA for 30 min to remove excessive biotin probe, re-dissolved in 1 ml of 0.2% SDS/PBS, and immunoprecipitated with 50 microliter anti-biotin agarose beads (Vector Laboratories) at room temperature for 1 h. Immunoprecipitates were then analyzed by SDS-PAGE and stained for visualization. Protein bands were excised from SDS-gel, extracted, reduced, alkylated, and trypsin digested to elute peptides and subjected to LC-MS/MS analysis for identifying peptide sequences in MS core in Genomics Research Center, Academia Sinica, Taipei, Taiwan.

Detection of CagA on protein blots: Protein extracted from control or alkynyl Fuc 1 analog-treated HC samples were subjected to cycloaddition labeling to label with biotin probe (protein 1 mg/ml with 0.1 mM azido biotin 6/0.1 mM Tris-triazoleamine catalyst/1 mM CuSO4/2 mM sodium ascorbate in lysis buffer), followed by immunoprecipitation with anti-CagA antibody (Santa Cruz). The derivatized alkynyl Fuc tags/biotin labeling on CagA protein were detected by peroxidase-conjugated streptavidin on protein blot.

Example 10

Pulse-Chase Analysis of Fucosylated and Sialylated Glycans

Cells of interest may be grown to log phase and then presented with various derivatized sugars for a limited period of time; for example, 30 minutes. After the limited period of time, the cells are no longer presented with the various sugars. The cells with glycoconjugates incorporating various tagged sugars may then be visualized over time through secondary detection/and or microscopy in relation to various intracellular and intercellular structures, in order to collect data on the trafficking and relative location of tagged and labeled glycoconjugates.

While various exemplary implementations of the present disclosure have been described in detail, it is apparent that modifications and adaptations of those exemplary implementations will occur to those skilled in the art. However, it is to be expressly understood that such modifications and adaptations are within the spirit and scope of the present disclosure.

All publications and patent applications cited in this specification are herein incorporated by reference as if each individual publication or patent application were specifically and individually indicated to be incorporated by reference.

We claim:

1. A composition comprising a tagged glycoconjugate wherein the tagged glycoconjugate is linked to a probe through a triazole moiety wherein the tagged glycoconjugate is provided by a process comprising:
   a) providing the L-enantiomer of the alkynyl derivatized sugar 1 having the structure

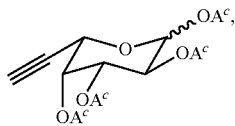

b) metabolically incorporating the alkynyl derivatized sugar 1 into a cellular glycan of a cell via the Fuc salvage pathway thereby producing a tagged glyconjugate in the cell wherein the tagged glycoconjugate comprises a glycan portion, a conjugate portion from the cellular glycan and the alkyne functional group from the alkyne derivatized sugar, and
   c) providing a probe having an azide group and linking the probe to the alkyne functional group of the tagged glycoconjugate through a triazole moiety by an azide-alkyne cycloaddition reaction to provide the tagged glycoconjugate linked to the probe through the triazole moiety.

2. The composition of claim 1, wherein the probe comprises a directly or indirectly detectable moiety.

3. The composition of claim 2, wherein the detectable moiety is selected from the group consisting of: a fluorescent moiety, a fluorogenic moiety, a moiety detectable by biotin-avidin interaction, a moiety detectable by antigen-antibody interaction, and a coumarin.

4. The composition of claim 3, wherein the probe comprises a fluorogenic detectable moiety which turns fluorescent upon Cu(I) catalyzed [3+2] azide-alkyne cycloaddition with the alkynyl functional group.

5. The composition of claim 3, wherein the probe comprises a N-alkyl-1,8-naphthalimide fluorogenic detectable moiety.

6. The composition of claim 1, wherein the resulting toxicity of the composition produced in claim 1 is improved by at least 10% as compared to presenting an azido-derivatized sugar to produce the tagged glycoconjugate.

7. A compound of the L-enantiomer of the alkynyl-derivatized sugar 1,

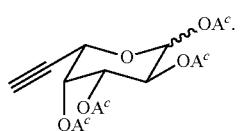

8. A kit comprising the compound of claim 7.

9. A composition comprising the L-enantiomer of the alkynyl-derivatized sugar 1,

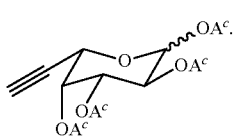

* * * * *

UNITED STATES PATENT AND TRADEMARK OFFICE
CERTIFICATE OF CORRECTION

PATENT NO. : 9,816,981 B2
APPLICATION NO. : 13/159339
DATED : November 14, 2017
INVENTOR(S) : Masaaki Sawa et al.

It is certified that error appears in the above-identified patent and that said Letters Patent is hereby corrected as shown below:

In the Claims

In Column 35, Lines 30-35, of Claim 1, " 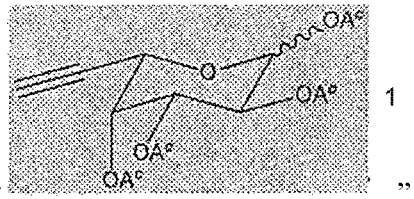 "

should be -- 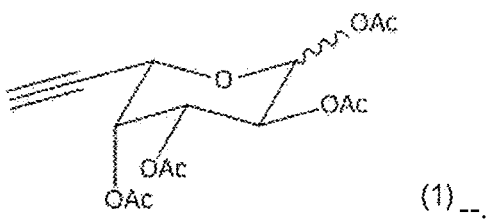 (1) --.

In Column 36, Lines 25-30, of Claim 7, " 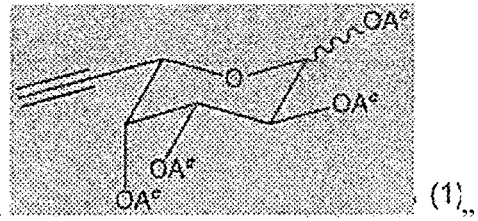 "

Signed and Sealed this
Twentieth Day of February, 2018

Andrei Iancu
*Director of the United States Patent and Trademark Office*

CERTIFICATE OF CORRECTION (continued)
U.S. Pat. No. 9,816,981 B2 should be -- 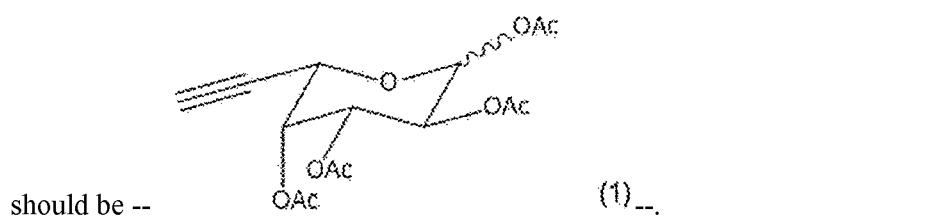 --.

In Column 36, Lines 35-40, of Claim 9, " 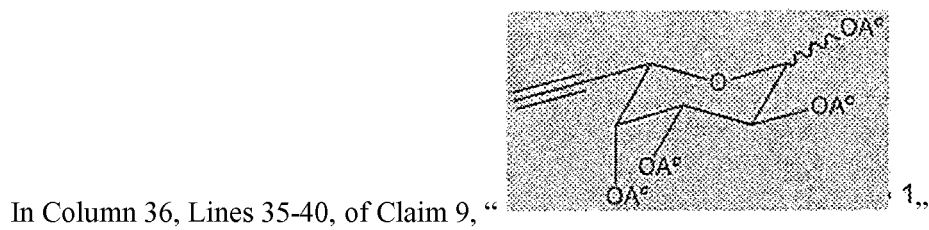 1,, should be -- 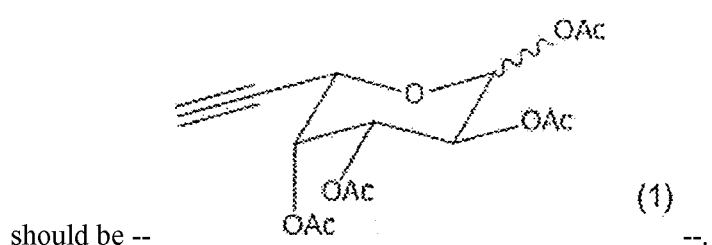 --.